United States Patent [19]

Joran

[11] Patent Number: 5,364,851

[45] Date of Patent: Nov. 15, 1994

[54] CONFORMATIONALLY RESTRICTED BIOLOGICALLY ACTIVE PEPTIDES, METHODS FOR THEIR PRODUCTION AND USES THEREOF

[75] Inventor: Alvin D. Joran, New York, N.Y.

[73] Assignee: International Synthecon, LLC, New York, N.Y.

[21] Appl. No.: 714,167

[22] Filed: Jun. 14, 1991

[51] Int. Cl.$^5$ .......................... C07K 1/00; C25B 3/00
[52] U.S. Cl. ..................... 530/345; 204/72; 204/78; 204/157.82; 530/303; 530/311; 530/312; 530/315
[58] Field of Search ............... 530/345, 402, 403, 333, 530/338, 303, 312, 311, 315; 930/320; 204/72, 78, 157.64, 157.82, DIG. 6

[56] References Cited

U.S. PATENT DOCUMENTS

| | | | |
|---|---|---|---|
| 3,446,789 | 5/1969 | Rudinger et al. | 930/320 |
| 3,816,385 | 6/1974 | Gillessen et al. | 530/315 |
| 4,191,754 | 3/1980 | Veber et al. | 530/311 |
| 4,485,039 | 11/1984 | Hruby et al. | 930/10 |

FOREIGN PATENT DOCUMENTS

| | | | |
|---|---|---|---|
| 292291 | 11/1988 | European Pat. Off. | 530/312 |
| 9783 | 10/1989 | WIPO | 530/333 |

OTHER PUBLICATIONS

Morikawa, et al., "Synthesis of EelCalcitonin and [Asu$^{1,7}$]-Eel Calcitonin: Contribution of the Disulfide Bond to the Hormonal Activty", *Experientia*, pp. 1104–1106, 1976.

Hase et al., "Synthesis of a Biologically Active Analog of Deamino-8-Arginine-Vasopress in which Does not Contain a Disulphide Bond", *Experientia*, 25, 1239–1240, 1969.

Nutt et al. "Useful Intermediates for Synthesis of Dicarba Analogues of Cystine Peptides: Selectively Protected α-Aminosuberic Acid and α,α$^1$-Diaminosuberic Acid of Defined Stereochemistry", *J. Org. Chem.*, vol. 45, No. 15, pp. 3078–3080, 1980.

Charpentier et al., "Cyclic cholecystokinin analogues with high selectivity for central receptors", *Proc. Natl. Acad. Sci. USA*, vol. 85, pp. 1968–1972, Mar. 1988.

Ho et al., "Synthesis of cyclic (Asu$^{1,7}$)-eel calcitonin by segment synthesis condensation on solid support", *Proc. Eleventh Amer. Peptide Symp.*, ed. by J. Rivier & G. Marshall (1990). ESCOM.

Veber et al., "Highly active cyclic and bicyclic somatostatin analogues of reduced ring size", *Nature*, vol. 280, pp. 512–514, Aug. 1979.

*Primary Examiner*—Jeffrey E. Russel

[57] ABSTRACT

Electrochemical methods, preferably the Kolbe coupling reaction, are utilized to create intramolecularly bridged peptides, segments or peptide isosteres which are conformationally restricted and preferably, biologically active. Preferably, the peptide analogues contain methylene groups bridging particular amino acid side chains. Analogues of a variety of peptide hormones, including insulin, insulin-like growth factors, somatostatin, melanocyte stimulating hormone, and the like are prepared by the above methods. Such peptides are useful as agonists or antagonists for treatment of diseases associated with deficiency of the hormone or dysregulation of hormone activity, as well as for mechanistic studies to understand the interactions between peptide hormones and cells.

16 Claims, 10 Drawing Sheets

↓ PdC/HCOOH/CH₃OH

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 4 amino acid
      ( B ) TYPE: amino acid
      ( D ) TOPOLOGY: linear ( i i ) MOLECULE TYPE: peptide ( x i ) SEQUENCE DESCRIPTION: SEQ ID NO:1:

Glu Gly Gly Glu
   1

( 2 ) INFORMATION FOR SEQ ID NO:2:

( i ) SEQUENCE CHARACTERISTICS:
      ( A ) LENGTH: 9 amino acid
      ( B ) TYPE: amino acid
      ( D ) TOPOLOGY: linear ( i i ) MOLECULE TYPE: peptide ( x i ) SEQUENCE DESCRIPTION: SEQ ID NO:2:

Glu Tyr Phe Gln Asn Glu Pro Lys Gly
   1               5

( 2 ) INFORMATION FOR SEQ ID NO:3:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Ala Gly Glu Lys Asn Phe Phe Trp Lys Thr Phe Thr Ser Glu
   1               5                   10

( 2 ) INFORMATION FOR SEQ ID NO:4:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Pro Ser Glu Thr Leu Glu Gly Gly Glu Leu Val Asp Thr Leu Gln Phe Val Glu
1               5                   10                  15

( 2 ) INFORMATION FOR SEQ ID NO:5:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Ser Tyr Ser Leu Glu Glu Phe Arg Trp Glu Lys Pro Val
   1               5                   10

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (D) OTHER INFORMATION: Leu-4 is Nle (xi) SEQUENCE DESCRIPTION: SEQ ID NO:6:

Ser Tyr Ser Leu Glu His Phe Arg Trp Glu Lys Pro Val
1              5                        10

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (D) OTHER INFORMATION: Glu-4 and Glu-10 are Dsu (xi) SEQUENCE DESCRIPTION: SEQ ID NO:7:

Ser Tyr Ser Glu Glu His Phe Arg Trp Glu Lys Pro Val
1              5                        10

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (D) OTHER INFORMATION: Glu-1 and Glu-4 are modified at
            their side-chains (ix) FEATURE:
        (D) OTHER INFORMATION: Glu-1 is modified at the amino
            end to add a Z group (xi) SEQUENCE DESCRIPTION: SEQ ID NO:8:

Glu Pro Gly Glu
1

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

Glu Glu Ala Ala Glu
1              5

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide ( x i ) SEQUENCE DESCRIPTION: SEQ ID NO:10:

Glu Phe Arg Ser Ala Asp Leu Ala Leu Leu Glu Thr Tyr Glu
1               5                   10

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( D ) OTHER INFORMATION: Glu-1 and Glu-4 are Dsu ( x i ) SEQUENCE DESCRIPTION: SEQ ID NO:11:

Glu Pro Gly Glu
1

CONFORMATIONALLY RESTRICTED BIOLOGICALLY ACTIVE PEPTIDES, METHODS FOR THEIR PRODUCTION AND USES THEREOF

BACKGROUND OF THE INVENTION

1. Field of the Invention

The invention in the field of peptide chemistry and medicine relates to novel conformationally restricted biologically active peptides and isosteres, methods for producing such peptides based on oxidative or reductive electrochemical coupling reactions, and methods of using such peptides as hormone agonists or antagonists in treating disease.

2. Description of the Background Art

A. Chemical Stabilization of Peptides

New methods for restricting the secondary structure of peptides and proteins are highly desirable for (1) basic structure-function studies, (2) the elucidation of mechanisms, and (3) the rational design of therapeutically useful conformationally-restricted (or "locked") pharmacophores.

These applications are exemplified by an analogue of eel calcitonin, [Asu$^{1,7}$]-eel calcitonin, in which α-aminosuberic acid (Asu) replaces the cysteine residues at positions 1 and 7 (Morikawa, T. et al., *Experientia* 32:1104–1106 (1976)). This analogue had significant biological activity, leading the authors to conclude that the disulfide bond in calcitonin is not essential for biological activity as long as the specific conformation of the peptide is maintained by an intramolecular bridge.

The purely chemical approaches for restricting secondary structure often requires extensive multistep synthetic work (Olson, G. L., *J. Am. Chem. Soc.* 112:323 (1990)). An alternative approach involves installing covalent bridges in peptides. However, due to the sensitivity of the peptide backbone and side chains, this method necessitates careful protection/deprotection strategies. For example, this problem occurs in the preparation of polymethylene analogues of [Arg$^8$]vasopressin in which α-aminosuberic acid (Asu) replaces the cysteine residues at positions 1 and 7 and in which the N-terminal amino group is removed (S. Hase et al., *Experientia* 25:1239–1240 (1969); S. Hase et al., *J. Amer. Chem. Soc.* 94:3590 (1972)), yielding deamino-dicarba-Arg$^8$-vasopressin.

Covalent linkages can, in selected instances, be established using other chemical methods, for example, by lactam formation between carboxylic acid and amine side chains (J. S. Taylor, *Acc. Chem. Res.* 23:338 (1990)), or by incorporation of pairs of Cys residues which form a disulfide bridge. However, these approaches suffer from disadvantages which the present invention has been designed to overcome in the creation of new cross-linked peptides.

B. Promotion of Peptide Secondary Structures

A number of approaches have attempted to induce α-helical secondary structures by the introduction of covalent bridges (Taylor, supra). Most of these procedures require an extensive synthetic effort as they involve constructing several intermediates typically, and require orthogonal protection strategies. The potential of intramolecular bridging in peptide design has become evident from recent studies on lactam-bridged amphiphilic structures (Taylor, supra).

For example, after synthesizing a protected peptide linked to an oxime polystyrene-resin through a glutamyl gamma-carboxyl side chain, an internal nucleophilic cleavage step generates the lactam ring and simultaneously frees the protected peptide. The utility of the lactam-bridging approach is exemplified by a 21-residue peptide prepared from three lactam-bridged units in series which exhibits unusually high α-helicity. This method is, however, cumbersome, and only allows covalent bridging on the hydrophilic side of an amphiphilic structure.

Another method, involving the metallation of an [i,i+4]-bishistidyl or [i,i+4]-histidyl-cysteinyl peptide, raises the α-helicity of the unmetallated sequence from about 54% to about 90% in 5 mM sodium borate buffer, pH 6.7 at 4° C. (M. R. Ghadiri et al., *JACS* 112:9633 (1990); S. Marqusee et al., *Proc. Natl. Acad. Sci. USA* 84:8898 (1987)). The use of toxic or heavy metals (e.g., $Cu^{+2}$, $Ru^{+2}$, $Cd^{+2}$) to induce helicity however makes the method less likely to find application in the design of clinically useful peptides.

C. Electrochemical Methods in Organic Chemistry

Electrochemical methods have a long history in organic chemistry and have recently found preparative application in the field of peptide synthesis (S. Coyle et al., *J. Chem. Soc., Chem. Commun.* 980 (1976)), largely limited to the installation or cleavage of protecting groups.

Using electrochemical methods, it is possible to convert selectively compounds with functional groups which differ in half-wave potential by approximately 200 mV (M. Baizer, ed., *Organic Electrochemistry*, 2nd ed., Dekker, New York (1983)). Chemical methods are not readily capable of the precision and extent of variability of redox potential that is essential for this selectivity.

Electrochemical methods generate reactive intermediates in concentration gradients which are highest near the surface of the electrode, whereas solution methods produce low steady-state levels of the intermediate species in the bulk medium (Baizer, supra). The high concentration of reactive intermediate at the electrode results in greater yields of coupling versus reaction with solvent or electrolyte (L. Eberson et al., In: M. Baizer, supra, p. 889; J. H. P. Utley et al., *J. Chem. Soc., Perkin Trans.* 2:395 (1978)).

One of the classic methods of organic electrochemistry is the Kolbe synthesis (Eberson et al., supra). In this reaction, the anodic oxidation of carboxylic acids produces hydrocarbon coupling products with the loss of carbon dioxide, often with excellent efficiencies. The reaction proceeds under acidic conditions to give free radical intermediates, which react to form either coupling products R—R,

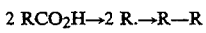

$$2\ RCO_2H \rightarrow 2\ R\cdot \rightarrow R\text{—}R$$

proton transfer, or disproportionation, while under basic conditions the anodic process generates carbenium ion intermediates, which yields nucleophilic addition products (H. -J. Schäfer, *Top. Cur. Chem.*, 152:91 (1990)).

By its nature, an electrochemical process involves molecules interacting at an electrode interface at which heterogeneous electron transfer takes place. After becoming loosely associated or perhaps adsorbed on the surface and being exposed to a sufficiently oxidizing or reducing potential, the most reactive functional group present in the molecule will form a reactive intermediate, such as a radical cation, radical anion, or free radical. Proton transfer may then follow, affecting the net charge of the reactive intermediate.

If a second reactive moiety is available at an appropriate distance and located on the same sterically accessible face of the molecule, coupling of the reactive intermediates will lead to bond formation. In the Kolbe method, two carbon free radicals join to form a new macrocyclic ring containing a carbon-carbon single bond. As long as the current density at the electrode is maintained at a sufficiently high level, the probability of forming two reactive intermediates in the same molecule within the lifetime of the first intermediate is reasonably high (Baizer, supra).

D. Electrochemical Reactions of Amino Acids and Peptides

Few precedents exist for the electrochemical transformation of protected amino acids and peptides under typical conditions common to other kinds of molecules (Schäfer, supra). Suberic acid derivatives, from which dicarba analogues of cystine-containing peptides have been obtained chemically (for example, oxytocin, calcitonin and somatostatin) have been prepared by Kolbe electrolysis of protected D-Glu and L-Glu (R. F. Nutt et al., *J. Org. Chem.* 45:3078 (1980)). There, the electrochemical reaction was performed on amino acids, not on a peptide. Electrochemical reactions of amino acids and peptides have been carried out at platinum, lead or glassy carbon electrodes, in solvents routinely used for organic electrochemistry such as methanol, acetonitrile, tetrahydrofuran, and N,N-dimethylformamide (Baizer, supra).

Classical studies by Takayama of the oxidation of simple amino acids in aqueous acid solutions, revealed that anodic electrolysis yields aldehydes resulting from loss of the carboxylic acid and primary e-amino groups. At alkaline pH, oxidation of amino acids yields nitriles as well as aldehydes, depending on the electrode used (Baizer, supra). These side reactions may have prevented the more widespread use of electrochemical reactions in peptide chemistry.

E. Peptide Hormones and Growth Factors

Peptide hormones are central to the regulation of metabolism, differentiation, proliferation, and growth. The relationship between peptide structure and activity remains best understood from studies of synthetic analogues designed to model biologically functional regions of the peptide. Direct structure-function correlation is rare due to difficulty in preparing crystals of intermediate-sized peptides of quality adequate for X-ray study.

There is a long-standing need in the art for a better understanding of how the conformational structure of a peptide modulates its regulatory role, in order to improve the prospect of treating or ameliorating diseases associated with defects or dysregulation of proteins such as growth factors and peptide hormones. A wide range of diseases, including cancer, osteoporosis, diabetes, and other metabolic defects, await the development of rationally designed agonists and antagonists to native polypeptide hormones. As chemical and electrochemical manipulation of peptide structure becomes a more precise science, the likelihood improves for major strides in the prevention and management of a multitude of diseases related to metabolism, cell development and differentiation.

1. Insulin and Insulin-Like Growth Factors

The development and application of insulin for the treatment of diabetes mellitus, the first example of a peptide pharmaceutical, is one of the great medical achievements of the twentieth century. Insulin is a 6 kDa peptide hormone made up of two chains, A and B, linked by a pair of disulfide bonds, and is derived biosynthetically from proinsulin which consists of A and B chains coupled by a third segment, designated C.

Glucose regulation, which is tightly correlated with normal development, is known to be associated also with other insulin-like peptide hormones (P. D. Gluckman, *Oxford Rev. Reprod. Biol.* 8:1 (1986)). Specific polypeptide hormone growth factors, like insulin, are now known to be critical in development (S. Heyner et al., In: *Growth Factors in Mammalian Development*, I. Y. Rosenblum et al. (eds), CRC Press, Boca Raton, Fla., 1989, pp. 91-112). The insulin-like growth factors, IGF-I (A. Ullrich et al., *EMBO J.* 5:2503 (1986)) and IGF-II (E. Rinderknecht et al., *FEBS Lett.* 89:282 (1978))), have extensive sequence homology with proinsulin. Computer modelling purports a similarity in the tertiary structures of IGFs and insulin (T. L. Blundell et al., *Nature* 287:781 (1980); T. L. Blundell et al., *Feder. Proc.* 42:2592 (1983)). X-ray crystal data are not yet available for IGF-I or IGF-II. All of these peptides have overlapping functions with differing activities at each other's receptor.

Insulin has also been found to play a central role in growth regulation as well (D. S. Straus, *Endocrinol. Rev.* 15:356 (1984)). Receptors which bind insulin and IGFs have been detected in early mammalian embryos. Both deficits and excesses of insulin have been correlated with birth defects (D. E. Hill, In: *The Diabetic Pregnancy: A Perinatal Perspective*, R. Merkatz et al., (eds) Grune & Stratton, New York, 1979, pp. 155-156). Nanomolar concentrations of insulin and IGF-I induce myoblast differentiation in chick embryos (C. Schmidt et al., *FEBS Lett.* 116:117 (1983)). Insulin also enhances neuronal proliferation (Garofalo, R. et al., *Molec. Cell. Biol.* 8:1638 (1988)). IGF-I and insulin are both able to stimulate RNA and protein synthesis (U. Widmer et al., *Acta Endocrinol.* 108:237 (1985)). Abnormally high levels of insulin or proinsulin have been found to cause abnormal growth, teratogenic effects, and death in chick embryos, possibly by interaction at the IGF receptor (F. DePablo et al., *Diabetologia* 28:308 (1985)).

2. Melanocyte Stimulating Hormone

Melanocyte stimulating hormone (MSH) is produced in the pituitary, and controls skin melanin dispersion (T. K. Sawyer et al., *Am. Zool.* 23:529 (1983); E. Schröder et al., In: *The Peptides: Synthesis, Occurrence, and Action of Biologically Active Polypeptides*, vol. 2, Academic Press, New York, pp. 165ff (1966)). The alpha, beta, and gamma forms of MSH are derived from the precursor proopiomelanocortin, which is also the source of adrenocorticotrophic hormone (ACTH) and the opioid peptide β-endorphin. MSH is thought to play a role in fetal growth and development (Sawyer et al., supra). For example, MSH has been detected in human and other mammalian fetal pituitary tissue (A. J. Kastin et al., *Acta Endocrinol.* 58:6 (1968)), and postulated to be central to the timing of human birth (R. E. Silman et al., *Nature* 260:716 (1976)). Fetal MSH is also important for prenatal growth (G. J. Boer et al., *Applications of Behavioral Pharmacology in Toxicology*, Zbinden et al. (eds), Raven Press, New York, p. 251, 1983). Removal of the fetal rat pituitary prevents the normal growth spurt between days 19 and 21, which can only be restored by exogenous administration of MSH. In addition, treatment with antibodies to MSH stunts the growth during this same interval. The importance of restricted conformation to function in MSH, as has been shown for other cyclic lactam analogues (see below), makes it a good system in which to apply the approaches of the present invention. To date, effective MSH receptor agonists and antagonists have depended on the use of D-amino acids, as in [Nle$^4$,D-Phe$^7$]-α-MSH (Schröder et al., supra; W. M. Westler et al., *J. Amer. Chem. Soc.* 110:6256 (1988)).

3. Cholecystokinins

The C-terminal peptide of cholecystokinin, known as CCK-8 (residues 26–33), is a hormonal regulator of pancreatic secretion and gallbladder contraction, as well as a neuropeptide (Charpentier, B. et al., *Proc. Natl. Acad. Sci. USA* 85:19681972 (1988)). Cyclization of the CCK-8 analogue, Boc-[2-aminohexanoic acid]CCK-(27–33), has been carried out using a fragment condensation method (Charpentier, B. et al., *J. Med. Chem.* 30:962–968 (1987)) in conventional chemical peptide synthesis. Two cyclic compounds having an internal amide bond between the side chain amino group of D-Lys-29 and either the β-carboxyl group of a D-Asp-26 residue or the α-carboxyl group of a D-Glu-26 residue were shown to have high affinity and selectivity for guinea pig brain CCK receptors.

SUMMARY OF THE INVENTION

A major objective of the present invention is the development of a general and practical method for restricting the secondary structure of peptides by introducing covalent bridges, and uses of these methods for the design and production of stable, highly active, therapeutically useful peptide hormone analogues.

In a preferred embodiment, it is an objective of the present invention to provide conformationally stable secondary or tertiary polypeptide structures, such as alpha helix, beta turn reverse turn, etc., by means of building blocks which are conformationally restricted to the desired structure by means of specific covalent bonds produced using electrochemical reactions.

The purely chemical approaches to installing covalent bridges in peptides often involve conditions which are too harsh for maintaining the integrity of the peptide backbone and side chains without special protection schemes. The present invention was conceived in part to overcome these difficulties. Because of the intrinsic redox-directed specificity of the method, the present inventor appreciated that organic electrochemistry offers great promise in the preparation of modified peptides.

A rapid general method for generating conformationally defined peptides, as described herein, allows the efficient production of a vast array of compounds which are useful in determining the molecular structures essential for signaling or promoting cell differentiation and development. Congenital abnormalities or other disease states associated with a molecular defect in a hormone receptor resulting in too high or too low affinity for the hormone would be treatable using peptide hormone analogues according to the present invention wherein the binding affinities or biological activities are determined and finely tuned by the engineered secondary structures.

The present inventor has utilized electrochemical methods to create intramolecularly bridged peptides or peptide segments for incorporation into the synthesis of a wide range of bioactive molecules. By removing a relatively small number of degrees of freedom from the biologically active peptide, it is possible to retain considerable levels of activity while at the same time reducing susceptibility to proteolytic degradation. Such stability to proteolysis is important for an effective half-life in the bloodstream upon in vivo administration.

The present invention is directed to a method for producing a conformationally restricted peptide or peptide isostere, comprising subjecting a peptide or peptide isostere having at least two amino acids or amino acid derivatives, the amino acids or amino acid derivatives having side chains which can be coupled by means of an electrochemical coupling reaction, to conditions sufficient to form a covalent bond between the side chains by means of an electrochemical coupling reaction. Where necessary, labile functional groups which are not intended to be involved in the electrochemical reaction are first protected to avoid side reactions.

In a preferred embodiment the electrochemical coupling reaction is an oxidative coupling reaction. In a more preferred embodiment of the above method, the peptide or isostere has at least two available carboxylic acid functional groups and the oxidative coupling reaction is the Kolbe reaction.

The present invention includes a method as above wherein the peptide or peptide isostere has at least two cysteine residues, wherein, prior to the forming step, two cysteine residues are replaced with amino acids or amino acid derivatives having side chains capable of undergoing the electrochemical coupling reaction such that the covalent bond is formed between the two replacement amino acids or derivatives.

In an embodiment useful for producing a stabilized alpha helical structure, the peptide or peptide isostere has at least five amino acids or amino acid derivatives, wherein two amino acids or derivatives at position i and position i+4 have side chains capable of undergoing an electrochemical coupling reaction such that a covalent bond is formed between them. Preferably, the amino acids or amino acid derivatives at positions i+1, i+2 and i+3 are selected so as to permit a well-defined alpha helical structure to be obtained upon the coupling reaction.

In another embodiment of the above method useful for producing a stabilized beta turn structure, the peptide or peptide isostere has at least four amino acids or amino acid derivatives, wherein two amino acids or amino acid derivatives at positions i and i+3 have side chains capable of undergoing an electrochemical coupling reaction such that a covalent bond is formed between them. Preferably, the amino acids or amino acid derivatives at positions i+1 and i+2 are selected so as to permit a well-defined beta turn structure to be obtained upon the coupling reaction. The amino acids at positions i+1 and i+2, respectively, are preferably selected from the group consisting of Gly-Gly, Gly-Pro and Pro-Gly.

In another embodiment, the peptide or isostere may have at least two available aromatic groups and the oxidative coupling reaction is the oxidative coupling of two aromatic rings.

In yet another embodiment, the peptide has an available aliphatic amine group and a second amine group and the oxidative coupling reaction is the oxidative coupling of an aliphatic amine with the second amine forming a diazo linkage.

In one embodiment, the electrochemical coupling reaction is a reductive coupling reaction.

In a preferred embodiment of the reductive reaction method, the side chains comprise available halo groups or available hydroxyl groups which are first converted into halo groups, and the coupling reaction is the reductive coupling of the two halo groups.

In another embodiment, side chains comprise hydroxyl groups which are first substituted with alkylsulfonyl or arylsulfonyl groups, preferably tosyl groups, and the coupling reaction is the reductive coupling of the two alkyl- or arylsulfonyl groups through an ether cross-linked bridge.

In another embodiment of the reductive method, the side chains comprise two nitrophenylalanine residues and the coupling reaction is the reductive coupling of the nitrophenylalanine residues into a diazo linkage.

The present invention provides a conformationally restricted peptide or peptide isostere having at least two amino acids or amino acid derivatives the side chains of which are linked by a covalent bond, wherein the covalent bond is other than a disulfide bond or a lactam formation between carboxylate and amine side chains, and the linked amino acid derivatives are not aminosuberic acid. Preferably, the peptide has biological activity.

In one embodiment, a peptide or peptide isostere comprises a tetrapeptide or tetrapeptide isostere having a conformationally restricted beta turn secondary structure, wherein the side chains of the amino acids or amino acid derivatives at positions 1 and 4 of the tetrapeptide or tetrapeptide isostere are linked by a covalent bond. Preferably, *the amino acids or amino acid derivatives at positions 2 and 3 are Gly-Gly, Gly-Pro or Pro-Gly, or derivatives thereof.

In another embodiment a peptide or peptide isostere comprises a pentapeptide or pentapeptide isostere having a stabilized alpha helical structure, wherein two amino acids or derivatives at positions 1 and 5 or the pentapeptide or isostere have side chains linked by a covalent bond. Preferably, the amino acids or amino acid derivatives at positions 2,3, and 4 of the pentapeptide or isostere are selected so as to permit a well-defined alpha helical structure.

In other embodiments, the peptide is any of the following: formula IV in FIG. 2 (SEQ ID NO:2); formula IV in FIG. 3 (SEQ ID NO:3); formula IV in FIG. 4 (SEQ ID NO:4 SEQ ID NO:10). formula II in FIG. 5 (SEQ ID NO:5), formula II in FIG. 6 (SEQ ID NO:6) and formula II in FIG. 7 (SEQ ID NO:7).

DESCRIPTION OF THE PREFERRED EMBODIMENTS

Figure 1:
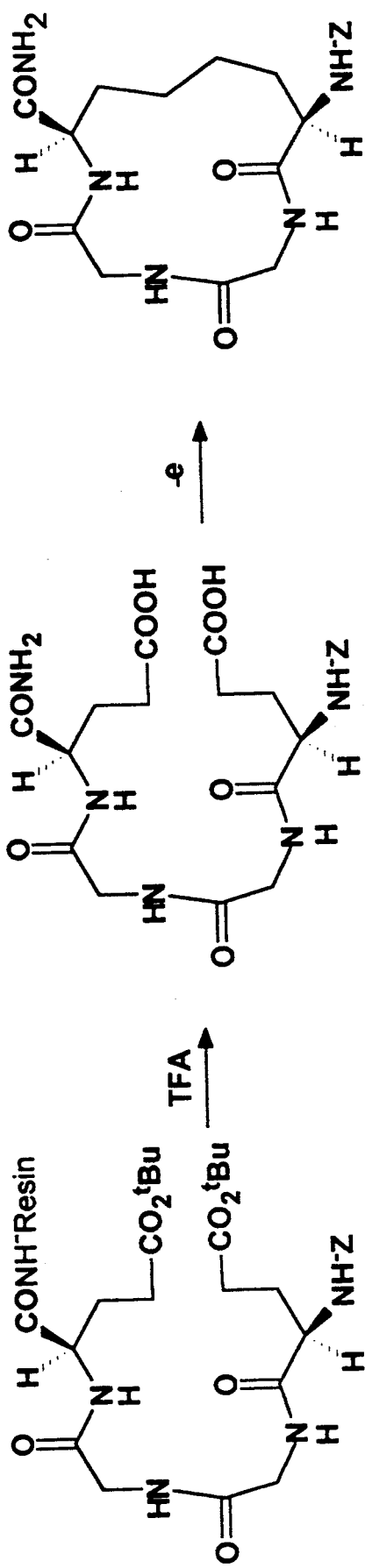
FIG. 1 shows the reaction sequence for producing a reverse turn subunit (SEQ ID NO:1).

The present inventor has conceived of a method for producing a conformationally restricted peptide or peptide isostere which preferably retains biological activity of the native peptide.

Such a peptide or isostere may be used to create a stable conformationally restricted structure, such as a helix or turn, or to otherwise restrict conformational mobility, where desired in the course of basic research into the structure and activity of polypeptides. Such a peptide may also be mass produced and used as a building block for incorporation in the synthesis of larger peptides and polypeptides for the same purpose.

Such a peptide or isostere, or larger polypeptides containing same, may also be used as an agonist to mimic the action of the peptide, or an antagonist to inhibit the action of the peptide. Thus, peptides and peptide isosteres produced according to the methods of the invention are useful as therapeutic agents for a variety of disease states associated with abnormal levels or actions of various biologically active peptides such as hormones. Thus, the peptides or isosteres of the present invention are useful either alone, or as a unit within a larger peptide.

The term "isostere" is defined in Korolkovas, A., *Essentials of Molecular Pharmacology: Background for Drug Design*, Wiley-Interscience, New York, 1970, p. 50. As used herein, a peptide isostere is intended to apply broadly to compounds or groups that are similar, according to the generally accepted view in the art, in their external electronic shells; the term also applies in a more restricted fashion to compounds or groups with similar localization of regions of high or low electron density in molecules of similar size or shape. According to Korokovas (supra) the term "classical isostere" refers to systems wherein peripheral electron layers are the same (for example, Cl, Br, I), or systems related by Grimm's hydrogen displacement law (for example, O, NH and $CH_2$) are proposed to have some similar properties. The term "nonclassical isosteres" refers to molecules whose steric arrangement and electronic configuration are similar, for example, —CO— and —$SO_2$—. As used herein, both classes of isosteres are intended. Thus, a peptide isostere as used herein is a peptide which may include natural amino acids, derivatives of amino acids, or structures which are generally not considered to be part of an amino acid or a peptide structure, but which have similar steric properties and electronic configuration. Examples of peptide isosteres known in the art are the hydroxyethylene dipeptide isosteres that act as non-hydrolyzable renin inhibitors (Evans. B. F. et al., In: *Peptides: Structure and Function*, Proc. 9th Amer. Peptide Symposium, C. M. Deber et al., eds, Pierce Chemical Co., 1985, p. 743).

By the term conformationally restricted is intended any peptide or isostere having a covalent bond which is either not present in the native peptide which it is intended to mimic, or is more stable than the bond which may already be present in the native peptide. This term may be exemplified by the placement of a single bond between the carbon atoms which in the native peptide are part of two separate side chain carboxylic acid functional groups, such as the omega-carboxylic acid groups of glutamic acid or aspartic acid. A further example is the substitution of Cys residues with other residues that may be bonded according to the present invention, thus replacing a more labile disulfide bond with a more stable C—C bond.

These conformationally restricted peptide units are designed to correspond to particular kinds of secondary structure or tertiary structure, including the α-helix, β-turn, and reverse turn. For a detailed description of secondary structure, see: G. E. Schulz et al., *Principles of Protein Structure*, Springer Verlag, New York 1985, in particular Chapter 6, pp. 108 et seq.; Creighton, T. E., *Proteins: Structure and Molecular Properties*, W. H. Freeman & Co., New York, 1983, in particular Chapter 6, pages 199 et seq. and Table 6-5. These references are hereby incorporated by reference in their entirety. Preferably, for maintaining a structure more stable than the native structure, for example, an α-helix, β-turn or β-meander, a covalent bond is introduced in place of the naturally occurring hydrogen bond, using the methods of the present invention. One of ordinary skill in the art will readily appreciate how to determine the sites in a peptide for introducing a covalent linkage in order to achieve the desired structural stabilization, without undue experimentation. It will also be apparent to one of ordinary skill in the art which amino acid substitution to make, and how to achieve protection and subsequent deprotection of the non-reacting sites, in order to practice the methods of the present invention.

Conformationally restricted peptides of the present invention can be peptides corresponding to an intact biologically active peptide, or to a fragment thereof. They may also be random peptide sequences created solely for the purpose of producing a particular secondary or tertiary structure for use in studying the effects of the conformation of larger polypeptides. For example, the peptides may be short sequences, such as 4 amino acids to create a β-turn or 5 amino acids to create an α-helical structure or an α-helix-promoting structure, which are later incorporated into larger peptides or protein analogues. In such short sequences, two particular residues, typically the terminal residues, are selected to permit the desired electrochemical reaction. However, the intervening amino acids can be more broadly and nearly randomly selected. Such selection will involve knowledge of the attributes of the specific amino acids, such as charge, size, known proclivity to enter into particular secondary structures, etc. However, such a short sequence need not be identical in sequence to a fragment of a known, biologically active peptide.

According to the present invention, the conformationally restricted peptide is produced by an electrochemical method, either oxidative or reductive. A preferred oxidative coupling reaction useful in the present invention is the Kolbe coupling reaction, which can couple omega-carboxylic acid moieties present in glutamic and aspartic residues within the peptide. Thus, as an initial strategy, the present inventor utilized intramolecular Kolbe coupling to couple two specifically positioned residues in a short peptide (see Examples below).

The methods of the present invention can be used for any peptide or isostere having at least two amino acid residues. Particular functional groups to be linked may be present naturally in the peptide, for example the carboxylic acid groups on the Glu or Asp side chain, or be introduced in the form of an "artificial" amino acid or an amino acid derivative, such as diaminosuberic acid, as discussed below.

For example, the secondary structure of vasopressin and somatostatin are each defined in part by a Cys-Cys disulfide bond. Replacement of this disulfide bond by a dimethylene bridge represents a conservative modification, and preserves biological activity.

In one embodiment of the present invention, the naturally occurring amino acids of the native peptide sequence are used to prepare precursors for electrochemical modification. This feature makes the approach of the present invention both convenient and inexpensive.

The economy of the methods of the present invention compared to prior art methods for the formation of a dimethylene bridge in a peptide can be readily appreciated by the following analysis. In the method of Hase et al. (supra) for preparation of a dicarba-Arg$^8$-vasopressin, the artificial amino acid Z-L-aminosuberic acid is required. This compound is sold by Peninsula Labs (1990–1991 price list) for $105 per gram. The actual reagent used in the prior art synthesis is Z-L-aminosuberic acid gamma-t-butyl ester, which must be protected by an additional four reaction steps and costs $145 per gram. In comparison, the reagent needed for the Kolbe method is Z-L-glutamic acid gamma-t-butyl ester, which is commercially available at $9 per gram (Bachem Bioscience, Inc.). Thus, the reagent alone as used in the method of the present invention represents a >95% savings in cost over the reagent used in the method of the prior art.

In other embodiments of the present invention, artificial amino acids are synthesized, using methods well-known in the art (see below), wherein these amino acids are specialized to exploit unique or useful reactivity properties of particular substituents such as halides and tosylates. Such modified amino acids may then be incorporated into a desired polypeptide, for example, during peptide synthesis, to create a starting material for an electrochemical reaction in accordance with the present invention.

Figure 9:
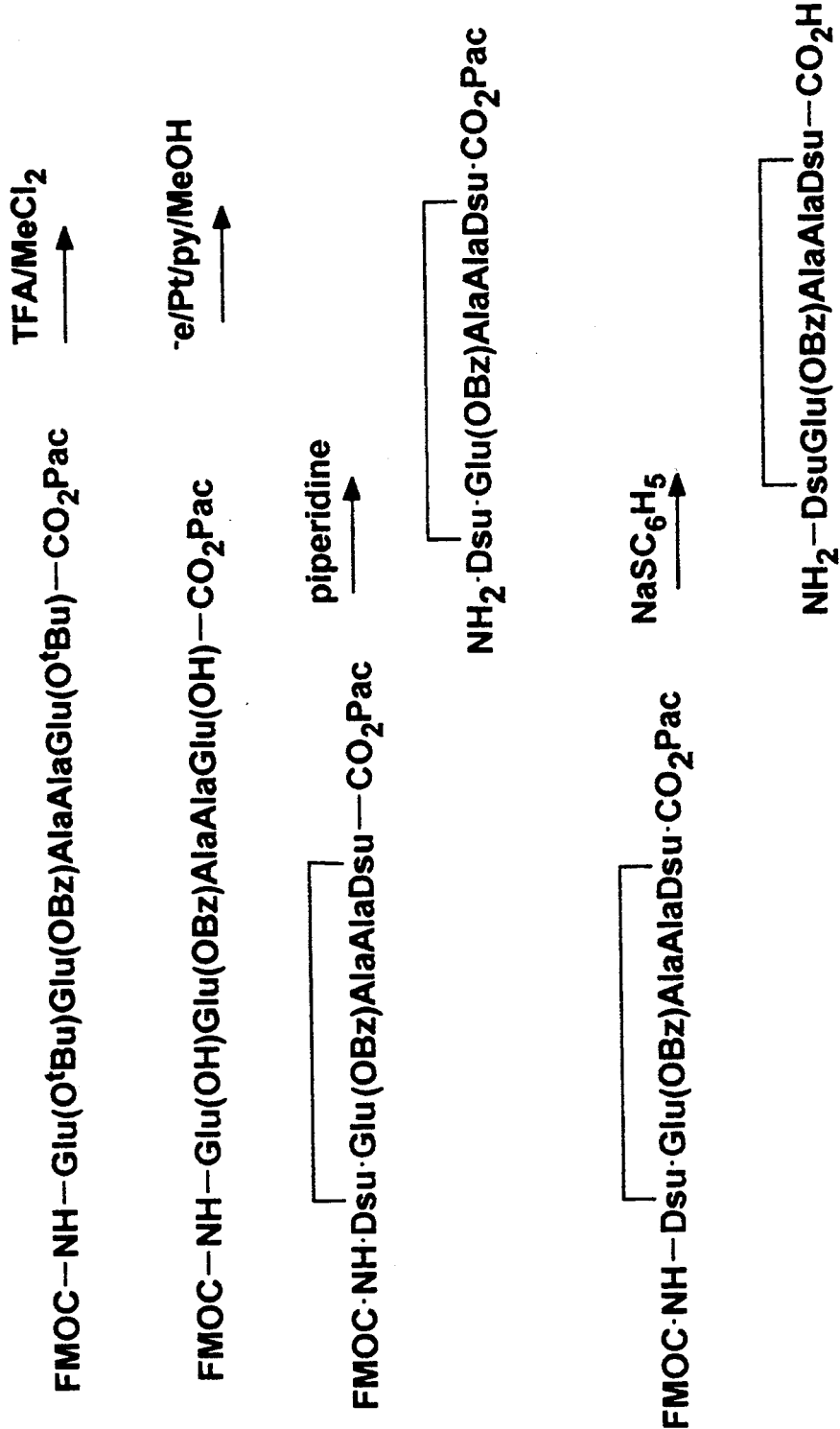
FIG. 9 shows the reaction sequence for synthesis of an α-helical fragment peptide (SEQ ID NO:9).

For example, in oligopeptides, conformationally locked secondary structure units may be prepared. By appropriate positioning of two latently reactive carboxylic acid side chains, Kolbe electrooxidative coupling would allow the formation of cross-linked α-helix (FIG. 9) or reverse turn structures (FIG. 1) which may then be manipulated as a building block in constructing larger polypeptide hormone analogues.

The strategy of electrochemical coupling of peptide fragments can be extended to encompass a large variety of types of coupling reactions in addition to the Kolbe synthesis. Among the possibilities of alternative coupling methods are such reactions as the coupling of an aliphatic amine with another amine to generate a diazo species (Fuchigami, T. et al., *Bull. Chem. Soc. Japan* 53:2040 (1980)), and the oxidative coupling of two aromatic rings (Bechgard, K. et. al., *Tetrahedron Lett.* 13:2271 (1972)).

In addition to oxidative electrochemical coupling, as described herein, methods based on reductive electrochemical coupling reactions may be used. For example, the electrochemical reductive coupling of alpha,omega-dihalides has generated nearly quantitative yields of strained rings (Fry, A. J. et al., *J. Org. Chem.* 38:2620 (1973)). Serine and threonine residues protected by acid labile t-butyl groups can be selectively deprotected during the acid cleavage from the 4-[2',4'-dimethoxyphenyl(aminomethyl)]phenoxy resin. The hydroxyl group can be readily converted to chloride or bromide using $P(C_6H_6)_3/CX_4$ or $P(C_6H_6)_3Br_2$ without disturbing the normal functionalities present in peptides. In an alternative strategy, the hydroxyls are tosylated with TsCl/pyridine, and then followed by the electrochemical reduction to install an ether cross-linked bridge. These reactions are illustrated in more detail in the Examples, below.

The methods of the present invention are useful in the study of all peptides having biological activity. Thus, the scope of this invention is unlimited. Specific examples of peptides on which work has already been conducted in accordance with the present invention, or which are candidates for such work, include: the developmentally relevant peptides nerve growth factor, insulin-like growth factors I and II, epidermal growth factor, human growth hormone, insulin and oncogene-encoded proteins. Other useful peptide targets for the electrochemical cross-linking methods of the present invention include vasopressin, which may be involved in brain development (D. De Wied, *Prog. Brain Res.* 60:155 (1983)), α-melanocyte stimulating hormone, which has been linked to fetal development (Sawyer et al., supra), somatostatin, which is known to inhibit the release of growth hormone (A. Gomez-Pan et al., *Clin. Endocrinol. Metab.* 12:469 (1983); P. Brazeau et al., *Science* 179:77 (1973)); and cholecystokinin peptides (Charpentier, B. et al., 1988, supra). Theoretically, however, the present invention is useful in the production of conformationally restricted peptides corresponding to every biologically active peptide.

Spectroscopic methods well-known in the art, including nuclear magnetic resonance, infrared spectroscopy, and circular dichroism, are used to reveal the detailed nature of the actual secondary structure of the modified peptide.

Nuclear magnetic resonance spectrometry is a powerful tool for peptide structure analysis. In the absence of diffraction-quality crystals, NMR offers the most precise method available for determining peptide structure, and will provide information on the nature of peptide structure most relevant to a dissolved state. NMR thus helps establish the detailed conformational structure in the neighborhood of the electrochemically coupled moieties. Two-dimensional NMR techniques have been successfully applied to peptides with molecular weight up to about 15 kDa, much larger than the peptides described in the Examples below, using a variety of pulse sequences (Westler et al., supra; C. Griesinger et al., *Amer. Chem. Soc.* 110:7870 (1988)). Techniques which have been exploited extensively to determine details about peptide structure utilize nuclear Overhauser enhancement effects which can provide information about interatomic distances and through-bond coupling parameters which can reveal dihedral angles between coupled atoms. Vicinal spin-spin coupling constants $^3J_{NH\alpha}$ provide a reliable basis for confirming secondary structures suggested by interproton distance maps (K. Wüthrich, *NMR of Proteins and Nucleic Acids*, Wiley-Interscience, New York, Chap. 9, 1986).

Direct evidence for the formation of a hydrogen-bonded network necessary for forming an α-helix or β-sheet is accessed from an examination of the backbone amide-proton exchange rates, as was achieved in studies of bovine pancreatic trypsin inhibitor (BPTI) (G. Wagner et al., *J. Mol. Biol.* 160:343-61 (1982)). A segment of α-helical secondary structure is expected to exhibit slow exchange rates for all residues in the sequence. Spin-lattice relaxation lifetime measurements describe the regions of the oligopeptide which are more rigid or more flexible.

Circular dichroism spectropolarimetric studies provide important information on the secondary structure of the oligopeptides of the present invention (A. Wollmer et al., In: *Modern Methods in Protein Chemistry*, Walter de Gruyter & Co., Berlin (1983)). Analysis of CD spectra by comparison with reference spectra of regular polypeptides or globular proteins which have been previously characterized by X-ray crystallographic methods allows the calculation, with varying degrees of success, of the observed spectra in terms of idealized α-helix, β-sheet, and random coil structures. The CD spectra of an idealized α-helix shows minima at 208 nm and 222 nm and a maximum at 195 nm, while the β-structure exhibits a minimum at 217 nm and the random coil has a minimum below 200 nm. Studies which examine the effect of concentration on CD spectra are used to determine any role of self-aggregation in the formation of secondary structure. CD spectra are measured in a variety of solvent conditions ranging from buffered aqueous systems to mixtures of water and miscible organic solvents such as trifluoroethanol (TFE). Hydrogen-bond disrupting solvent systems should produce mainly unordered structures, while the increasingly hydrophobic solvents, which have been suggested to mimic the dielectric environment within a globular protein, should progressively accentuate the formation of helical structure (J. W. Nelson et al., *Proteins* 1:211 (1988)). Several computer programs are available which permit straightforward analysis of CD data by such methods (S. W. Provencher et al., *Biochemistry* 20:33 (1981); J. P. Hennessey et al., *Anal. Biochem.* 125:177 (1982); N. Greenfield et al., *Biochemistry* 8:4108 (1969)), affording semi-quantitative determinations of the proportions of secondary structural types.

Induction of the biologically active conformation is thought to result from interaction with the membrane-bound receptor surface (E. T. Kaiser et al., *Science* 223:249 (1984)). The air-water interface has been extensively studied as a convenient model for simulation of the physical interactions of biological interfaces (B. R. Malcolm, *Progress in Surface and Membrane Science*, Academic Press, New York, pp 189-229 (1973)). The behavior of peptides at the air-water interface characterizes the specific type of secondary structure hypothetically induced (or otherwise present) at the receptor surface. Peptides containing amphiphilic α-helical and β-strand structures form stable monolayers on buffered Langmuir troughs, which on compression produce clearly distinguishable pressure/area ($\pi$-A) isotherms (Malcolm, supra). Fitting the isotherm data to the two-dimensional equation of state $\pi[A-A_o(1-k\pi)]=nRT$, where $A_o$ is the limiting area at $\pi=0$, and k is the compressibility constant. Helices tend to be more compressible and less aggregated than β-strands. Film balance data are invaluable especially for comparing the interactions of the hormone analogs of the present invention with native peptide hormones.

There have been few studies of the β-turn secondary structure or models of β-turns at the air-water interface, and therefore the peptides of the present invention incorporating such turns will be useful for obtaining such information. A theoretical model for vasopressin interaction with its receptor incorporates both a hydrophobic and hydrophilic surface (Smith, G. W., *Dev. Endocrinol.* 13:23 (1981)), leading to the expectation that the structure is amphiphilic.

The biological activity of each internally cross-linked peptide hormone analogue may be examined in a variety of assays. Novel cross-linked peptide hormone analogues will be examined for either agonist and antagonist properties.

The activity of peptide hormones which act by stimulating the second messenger cyclic adenosine-5'-monophosphate (cAMP) is determined by their ability to stimulate cAMP formation in vitro using preparations of membrane-bound adenylyl cyclase using the standard $^3H/^{31}P$ double-label protocol (Y. Salomon et al., Anal. Biochem. 58:541 (1974)). The activity and specificity of vasopressin analogues is evaluated at V1 and V2 receptors.

The effects of growth factor analogues on embryogenesis is preferably assessed using rat embryonal carcinoma (EC) cell lines, which mimic the early morphological and biochemical stages of mammalian development in vitro (G. R. Martin, Science 209:768 (1980)). Analogues of IGF-I, IGF-II or MSH analogues are examined for activity in this way.

Somatostatin analogues are assayed for inhibition of the release of growth hormone (P. Brazeau, et al., Science 179, 77 (1973)).

Active compounds are tested for their susceptibility to enzymatic proteolytic degradation processes using methods well-known in the art. For example, see: Veber, D. F., et al., Nature 280:512 (1980)).

The preclinical and clinical therapeutic use of the present invention in the treatment of disease or disorders will be best accomplished by those of skill, employing accepted principles of diagnosis and treatment. Such principles are known in the art, and are set forth, for example, in Braunwald, E. et al., eds., Harrison's Principles of Internal Medicine, 11th Ed., McGraw-Hill, publisher, New York, N.Y. (1987).

The peptides and compositions of the present invention are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

Thus, the present invention provides a method for treating a subject in need of treatment with a peptide hormone agonist or antagonist. Using methods described herein, or other methods well-known in the art for establishing biological activity of a peptide hormone, one or ordinary skill in the art will be able to determine without undue experimentation the agonist or antagonist activity of a peptide hormone analogue according to the present invention. Such a peptide hormone analogue may then be administered to a subject having a deficiency or dysregulation in the activity of the peptide hormone, in order to treat such a deficiency or dysregulation.

By the term "treating" is intended the administering to subjects of peptide according to the present invention for purposes which may include prevention, amelioration, or cure of disease associated with a deficiency in a peptide hormone or dysregulation in the activity of the hormone.

According to the present invention, a subject, preferably a mammalian subject, more preferably a human, is treated with a peptide according to the present invention. Such treatment may be performed alone or in conjunction with other therapies.

The present invention thus includes pharmaceutical compositions containing the peptide of the present invention along with a pharmaceutically acceptable excipient. Also included is a pharmaceutical composition comprising the peptide, in combination with an additional therapeutic agent plus a pharmaceutically acceptable excipient.

In addition to the pharmacologically active compounds, the pharmaceutical compositions of the present invention may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

To enhance delivery or bioactivity, the peptides can be incorporated into liposomes using methods and compounds known in the art.

The peptides are formulated using conventional pharmaceutically acceptable parenteral vehicles for administration by injection. These vehicles are nontoxic and therapeutic, and a number of formulations are set forth in Remington's Pharmaceutical Sciences, 16th ed., Mack Publishing Co., Easton, Pa. (1980). Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

The peptides of the invention are preferably formulated in purified form substantially free of aggregates and other protein materials, preferably at concentrations of about 1.0 ng/ml to 100 mg/ml.

A typical regimen for treating a peptide hormone deficiency, for example, comprises administration of an effective amount of the appropriate conformationally-restricted peptide agonist administered over a period of one or several weeks and including between about one and six months.

The peptide of the present invention may be administered by any means that achieve its intended purpose. For example, administration may be by various parenteral routes including subcutaneous, intravenous, intramuscular, intraperitoneal, intradermal, transdermal, intracerebroventricular, intrathecal or buccal routes. Alternatively, or concurrently, administration may be by the oral route. Parenteral administration can be by bolus injection or by gradual perfusion over time.

It is understood that the dosage of peptide administered will be dependent upon the age, sex, health, and weight of the recipient, kind of concurrent treatment, if any, frequency of treatment, and the nature of the effect desired. The ranges of effective doses provided below are not intended to limit the inventor and represent preferred dose ranges. However, the most preferred dosage will be tailored to the individual subject, as is understood and determinable by one of skill in the art.

The total dose required for each treatment may be administered by multiple doses or in a single dose. The peptide may be administered alone or in conjunction with other therapeutics directed to the treatment of the deficiency or dysregulation.

Effective amounts of the peptide are from about 0.01 μg to about 100 mg/kg body weight, and preferably from about 10 μg to about 50 mg/kg body weight.

Having now generally described the invention, the same will be more readily understood through reference to the following examples which are provided by way of illustration, and are not intended to be limiting of the present invention, unless specified.

EXAMPLE I

Intramolecular Electrochemical Coupling of Precursor Peptide Hormones and Structure Fragments The general synthetic strategy will include:
(1) preparation of an oligopeptide sequence containing the latent electrochemically reactive moieties in a form protected for the duration of the chemical steps leading up to the coupling event;
(2) inducing the electrochemical coupling under structure promoting conditions such as solvents which stabilize hydrogen bonds, for example, trifluoroethanol; and
(3) deprotecting all orthogonally protected functional groups.

Larger peptide hormones are likely to have many different labile side groups not compatible with either peptide coupling reactions or electrochemistry. A sufficient variety of protecting groups are now available which are stable both to the FMOC protocols and to the electrooxidation and electroreduction conditions.

Figure 2:
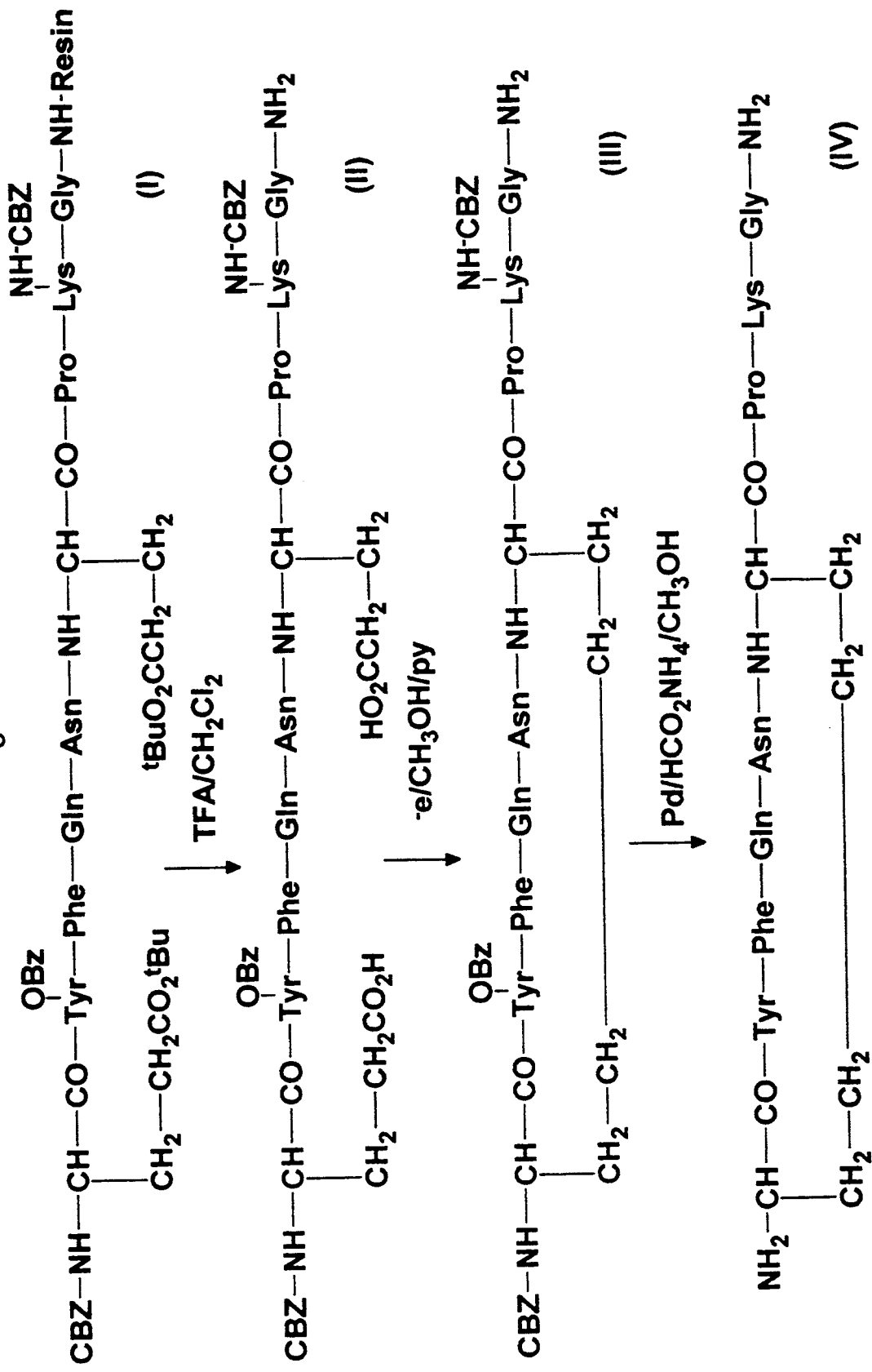
FIG. 2 shows an efficient route to synthesis of [Dsu[1,6],Lys[8]]vasopressin (SEQ ID NO:2).

An example which will demonstrate the ease and utility of the approach is the nonapeptide hormone [$^8$Lys]-vasopressin, which contains a disulfide bridge linking cysteines at positions 1 and 6 (FIG. 2). Exchange of the cysteine residues with gamma-t-butyl glutamyl residues, followed by the standard electrochemical coupling protocol, will result in the convenient replacement of the sulfur atoms of the cystine bridge with isosteric methylenes. The crude cross-linked peptide will be purified by size-exclusion chromatography (to eliminate intermolecularly coupled dimeric products) and by high performance liquid chromatography (HPLC).

The conformationally restricted peptide units, as prepared, will contain protecting groups at the N-terminus and all reactive substituents, and will thus be in a form suitable for incorporation into an elongating polypeptide chain using standard methods of solid-phase fragment condensation (Kaiser, E. T., et al., *Science* 243:187 (1989)). Progress in fragment coupling is analyzed by amino acid analysis. After the conformation-restricting fragment is incorporated, the remaining individual residues of the sequence are incorporated using Merrifield or Sheppard methods (E. Atherton et al., *J. Chem. Soc., Chem. Commun.* 537 (1978)).

The identity of each peptide analogue prepared by the new cross-linking method of the present invention will be confirmed by amino acid analysis and by electrospray ionization mass spectrometry or fast atom bombardment mass spectrometry. Prior to incorporation into the synthesis of peptide analogues, the fragments will be examined by a variety of spectroscopic techniques including circular dichroism and nuclear magnetic resonance spectroscopy in order to determine the conformational structure which was stabilized as a result of the electrochemical process. By an iterative procedure, it will be possible to fine tune the nature of the conformational restriction by conducting the electrochemical process under altered conditions, or by selecting different positions for the electroactive residues.

EXAMPLE II

Preparation of a Tetrapeptide With a β-Turn

Tetrapeptides having a β-turn was prepared according to the following scheme (see FIG. 1):

A. Z-Glu-(gamma-O-t-Bu)-Gly-Gly-Glu-(gamma-O-t-Bu) (SEQ ID NO:1)
  (1) synthesis of an N-protected sequence -Glu-(gamma-O-t-Bu)-Gly-Giy-Glu-(gamma-O-t-Bu) (SEQ ID NO:1) on the 2',4'-dimethoxy-4-benzhydrylamine resin using 9-fluorenylmethoxycarbonyl (FMOC) protocols (Fields, G. B., *Int. J. Peptide Prot. Res.* 35:161 (1990)).
  (2) cleavage with trifluoroacetic acid to give Z-NH-Glu-Gly-Gly-Glu-NH$_2$ (SEQ ID NO:1); and
  (3) electrochemical oxidative coupling at a platinum gauze electrode at 0°–5° C. in methanol/pyridine.

The reaction proceeded cleanly to give the desired product, with only minor side products, as indicated by thin layer chromatography.

The cross-linked tetrapeptide showed an interesting concentration dependence, indicating an increasing extent of self-association as the concentration increased. This suggests the possible formation of a more extended β structure.

Circular dichroism spectra were measured in aqueous KF and phosphate buffers, and exhibited minima varying between 209 nm and 218 nm, and between 185 and 195 nm, at concentrations between 0.1 and 35 μM. These spectral features resemble characteristics found in previous model type I and II' β-turns (R. W. Woody, In: *The Peptides: Analysis, Synthesis, Biology*, vol. 7, V. Hruby (ed), Academic Press, New York, 1985, Chapter 2).

[Leu]Enkephalin, the X-ray crystal structure of which demonstrates the presence of a type III' β-turn (G. D. Smith et al., *Science* 199:1214 (1978)), shows similar signs of association by CD and NMR at millimolar concentrations in DMSO and TFE (M. A. Khaled et al., *Biochem. Biophys. Res. Comm.* 76:224 (1977)).

The cross-linked tetrapeptide containing Gly$^2$-Gly$^3$, the most conformationally flexible residue combination, generates a structure with moderately restricted conformation according to CD. A negative band at 191 nm did not change with concentration, while a second negative band shifted position from 216 nm at low concentration to 208 nm at high concentrations, suggesting the contribution of mobile or distorted β-turns susceptible to polar solvent disruption.

B. Z-Dsu-Pro-Gly-Dsu (SEQ ID NO:11)

Figure 8:
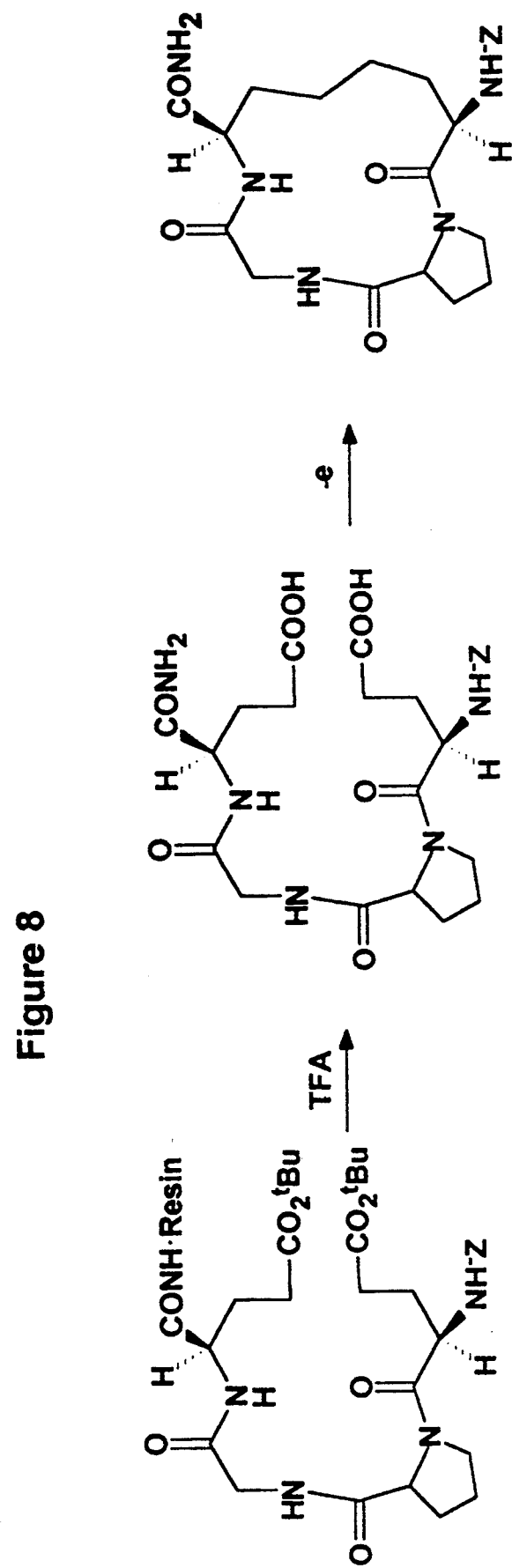
FIG. 8 shows the reaction sequence for preparing a tetrapeptide beta turn (SEQ ID NO:8 SEQ ID NO:11).

A second tetrapeptide having a well-defined β-turn due to the replacement of Gly$^2$ with Pro, a residue with high propensity to form turns in native globular proteins was also synthesized. The Z-Dsu-Pro-Gly-Dsu (SEQ ID NO:11) cross-linked between the Dsu residues was synthesized as follows (FIG. 8).

Twenty mg of the linear peptide was dissolved in 10 ml methanol (freshly distilled) in a 50 mL glass beaker. To this was added 76 μl of triethylamine and 0.9 mg of metallic sodium. The beaker was charged with two wire mesh platinum electrodes and a calomel reference electrode. The reaction mixture was placed in an ice water bath and charged at constant voltage +2.8 V, using a Model 363 EG&G Potentiostat/Galvanostat for a period of 60 minutes. The initial current which was at 0.8 A fell to 0.02 A in that period. The current was monitored for another 1 hour and showed no detectable decrease. Thin layer chromatography (TLC) of the reaction mixture on silica gel (plastic, coated with UV 254+ material) gave one PMA positive spot with an $R_f$ of 0.32 (chloroform/ethyl acetate, 95/5). The starting material appears on the baseline in this solvent system. The starting material was earlier tested for purity by TLC in n-butanol/acetic acid/water 4/1/1 and gave one spot with an $R_f$ of 0.45.

The reaction mixture was then poured into a round bottom flask and solvent was removed under reduced pressure to give 12 mg of a dark brown viscous oil. HPLC analysis of an aliquot of this material (in acetonitrile), using a C18 (Vydac, 300 Å) reverse phase column showed presence of the starting material $r_t$ 20 min. and two other peaks at $r_t$ 24 min. (analyzed to be two materials eluting very closely) and $r_t$ 32.5 min. The fraction eluting at 32.5 min was collected an analyzed for amino acid content and gave Gly (1.00) to Pro (1.00) showing no presence of glutamic acid. The crude product from the electrochemical step was taken up in chloroform/ethyl acetate (95/5) and washed with 10% sodium carbonate solution and 0.5M citric acid solution. The organic layer was washed with saturated sodium chloride solution and dried over anhydrous magnesium sulfate and filtered. Upon removal of the solvent, a colorless filmy material (10 mg) was obtained. This material was taken up in acetonitrile/water 50/50 and analyzed using a C18 reverse phase column, using isocratic conditions (50% acetonitrile/water/0.1% TFA) over 30 minutes, showing that much of the starting material and by-products were removed by the workup procedure. The crude product was taken up in the minimal amount of acetonitrile/water (1:1) and purified using a C18 10μ pore-size reverse phase column using isocratic conditions 50% acetonitrile/water. The fraction eluting at $r_t$ 34 min was collected and, after removal of volatile solvents, was lyophilized to give 4 mg of a white flaky solid that was submitted for FAB mass spectroscopy: M+ 473 (calculated, 473). Amino acid analysis by reverse phase HPLC after hydrolysis of an aliquot of the peptide in propionic acid/HCl (1:1) at 150° C. for 45 min showed the absence of any Glu in the product, though the analysis gave responses for the PTC derivatives of Pro and Gly.

Upon analysis by circular dichroism (as above), the Pro-Gly tetrapeptide showed a stable negative band at 193 nm, unaltered by concentration (3.7-346 μM, 0.01M KF). When dissolved in trifluoroethanol, the cross-linked Pro-Gly system develops a stronger negative band at 190 nm and small positive bands at 202 nm and 220 nm. This spectrum agrees well with theoretical spectra for β-turns (Chang et al., *Anal. Biochem.* 91:13 (1978)).

C. Reverse Turn Subunit

A coupling sequence as shown in FIG. 1 will be used to establish a reverse turn subunit. This reaction involves (1) preparation, on a 4-[2',4'-dimethoxyphenyl-(aminomethyl)]phenoxy resin (e.g., see: H. Rink, *Tetrahedron Lett.* 28:3787 (1987)) of a tetrapeptide consisting of two benzyl ester-protected gamma-glutamates separated by two "spectator" residues (glycines);

(2) cleavage from the resin with trifluoroacetic acid; and (3) subsequent electrochemical cross-linking in pyridine-methanol at pH 7.0.

A tetrapeptide such as the ones described above may contain any amino acid in position 2 and 3 that is consistent with the secondary structure desired. Preferably, the amino acid residues in these positions are Gly-Gly, Pro-Gly or Gly-Pro, consistent with achieving a stable beta turn. Such a structure can be utilized according to the present invention as a building block for a conformationally stable analogue of any peptide known or proposed to have a beta turn as a structural element which is important for its biological activity. Many peptides with beta turns are known in the art, for example the antibiotic gramicidin and the hormone vasopressin (see below).

EXAMPLE III

Synthesis of [Dsu$^{1,6}$,Leu$^8$]Vasopressin

A. Z-Glu-Tyr(OBz)-Phe-Gln-Asn-Glu-Pro-Leu-Gly-NH2 (SEQ ID NO:2)

The linear peptide [Glu$^{1,6}$,Tyr(OBz)$^2$,Leu$^8$]vasopressin was synthesized on a 4-[2',4'-dimethoxyphenyl(methylamino)]phenoxy resin using FMOC amino acid active esters. The first amino acid was introduced on the solid-phase support by coupling with dicyclohexylcarbodiimide (DCC) and diisopropylethyl amine (DIEA) in methylene chloride/dimethyl formamide (1:1). The reaction was monitored till no more free amine was detectable by the Kaiser test. The determination of the substitution level was carried out by cleaving the FMOC group from an aliquot of the resin-amino acid and determining the optical density of the liberated fluorene the substitution level of the first amino acid loaded was 0.23 mmol/g. The remaining residues of the peptide were added using five equivalents of the FMOC-amino acid active ester, prepared separately by reacting the FMOC-amino acid with diisopropyl carbodiimide and hydroxybenzotriazole in methylene chloride/dimethyl formamide (1:1) for one hour at 0° C. The FMOC group was cleaved using piperidine (50% in dimethyl formamide). The glutamic acid residues were introduced with side chain acid functions protected with t-butyl groups in order to facilitate simultaneous deprotection with the cleavage of the peptide from the resin. Tyrosine was introduced with the phenyl O-benzyl protected. The N-terminal amino acid (glutamic acid) was introduced as the N$^\alpha$-benzyloxycarbonyl (Z) derivative. The finished peptide was cleaved from the resin using trifluoroacetic acid (50% in methylene chloride). The resin was subsequently washed with TFA (20% in methylene chloride). The peptide solution in TFA and methylene chloride was filtered, and the volatile solvents were removed under reduced pressure to give a dark viscous oil which was taken up in 25 mL 50% acetonitrile/water. After removal of acetonitrile under reduced pressure, the water suspension of the peptide was lyophilized to give 800 mg of crude peptide, a flaky yellow powder. Four hundred milligrams of the linear diacid crude peptide were dissolved in 20 mL of 50% acetonitrile/water and analyzed by HPLC (Vydac, C18 reverse phase, 300 A, 4.6×250 mm, A: 0.1% TFA/water, B: 0.1% TFA/acetonitrile, 0–50% B linear gradient over 30 min). The fraction eluting at 16.12 minutes possessed an amino acid analysis corresponding to the expected product. The bulk of the sample was purified on a semi-preparative HPLC column (Vydac, C18 reverse phase, 300 A, 10×250 mm, A: 0.1% TFA/water, B: 0.1% TFA/acetonitrile, 0–50% B linear gradient over 30 min). Fractions were pooled together, and after removal of volatile organic solvents, the water suspension of the peptide in water was lyophilized to give 126 mg of a flaky white solid.

B. [Dsu $^{1,6}$,Leu$^8$] Vasopressin

Five milligrams of the linear diacid peptide amide were dissolved in 10 mL methanol/pyridine (3:1). To this was added 4.3 mg of sodium methoxide and 0.1 mg sodium metal in a 50 mL glass beaker. The glass beaker was fitted with two cylindrical wire mesh platinum electrodes and placed in an ice water bath. The cell was charged at +2.8 V (relative to a standard calomel reference electrode) for one hour. TLC on silica gel showed the presence of a substance faster moving than the starting material in n-butanol/acetic acid/water (3:1:1; Rf=0.63), and stains PMA positively. The initial current was 750 mA, which had fallen to 25 mA in this time. The reaction was allowed to go for another one hour at which point the current fell to 20 mA. After 4.4 hours the current reached a saturation value of 20 mA, and did not decrease further. The reaction mixture was poured into a tared round bottom flask and the volatile solvents were removed under reduced pressure. The viscous oil that was obtained was taken up in 20 mL chloroform/ethyl acetate (95:5), filtered, and washed with 10% sodium carbonate solution (2×20 mL) and 0.5M citric acid solution (2×20 mL). The organic layer was then washed with saturated sodium chloride solution (2×10 mL) and dried over anhydrous sodium sulfate. After removal of solvent, a brown powdery solid was obtained. This solid was taken up in 10 mL acetonitrile and water (1:1) and analyzed by HPLC (Vydac C18, 300 A column, 4.6×250 mm, 50% acetonitrile/water, isocratic, 1.2 mL/min) which showed the presence of one major component at 34.5 min. The crude peptide was purified by HPLC (Vydac C18, 300A, 10×250 mm, 50% acetonitrile/water, isocratic, 3 mL/min). After removal of volatile solvents from the pooled fractions the aqueous suspensions were lyophilized to give 2.3 mg of a flaky white solid. The fraction eluting at 34.81 min was collected and analyzed by fast atom bombardment was mass spectroscopy demonstrating the presence of M+ 1213.5 (calculated, 1213.5). A small amount of this sample was dissolved in 100 μL of acetonitrile and analyzed on a Vydac C18 analytical column under isocratic conditions (50% acetonitrile in water, 40 minutes), and was found to be homogenous.

EXAMPLE IV

Figure 3:
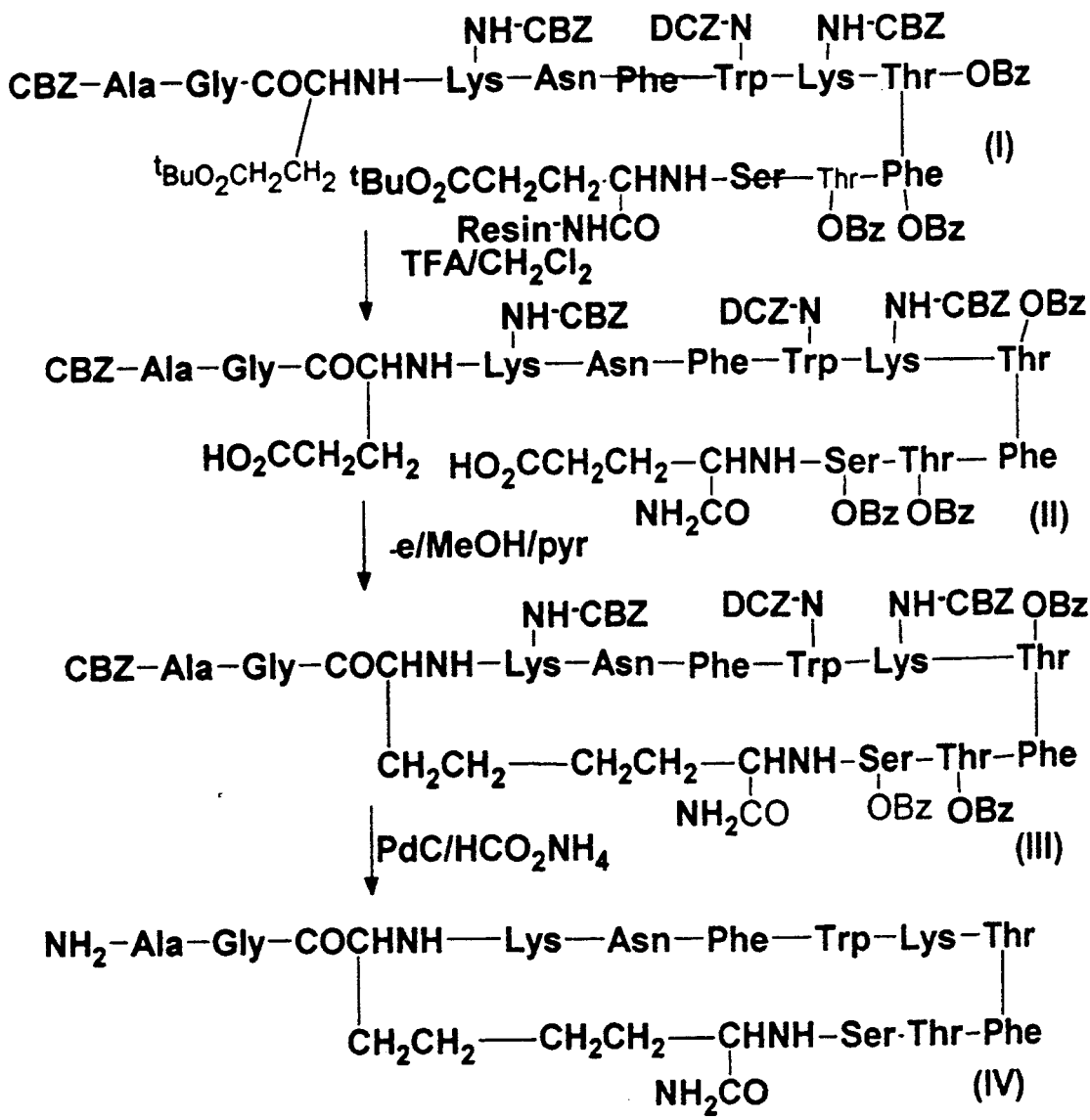
FIG. 3 shows the reaction sequence for synthesis of [Dsu[4,15]]somatostatin-(2-15) (SEQ ID NO:3).
Figure 4A:
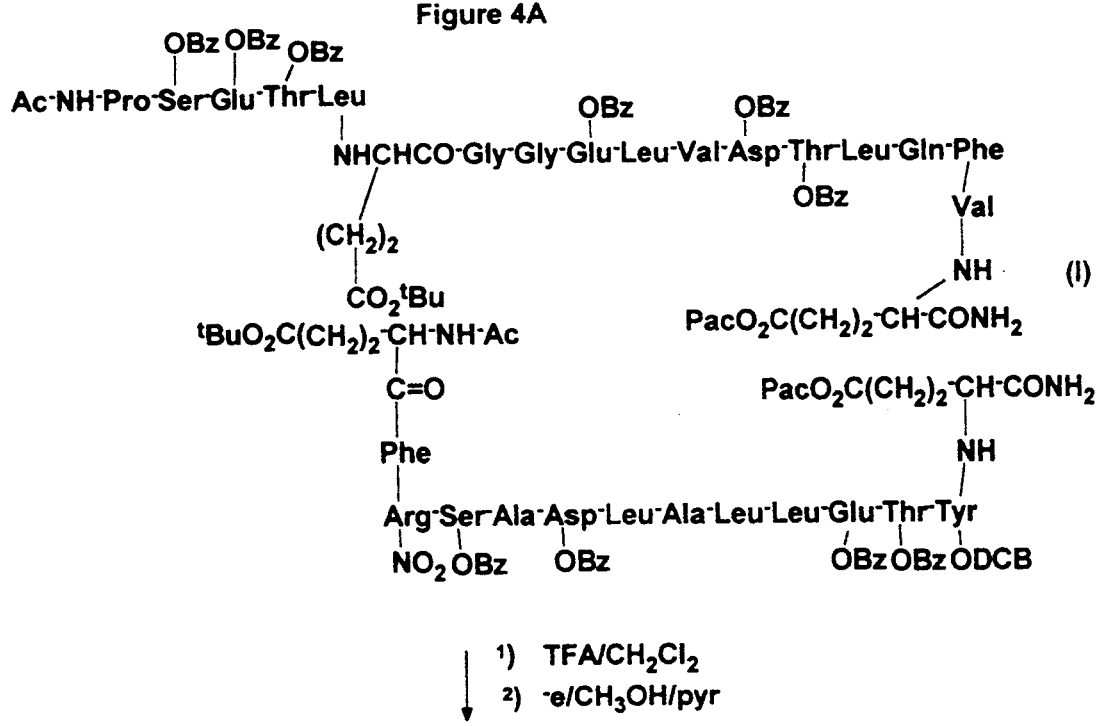
FIG. 4A-B as reaction steps (I)-(IV) shows the reaction sequence for synthesis of a two-chain bis(dicarba) IGF-II peptide (SEQ ID NO:4 SEQ ID NO:10).
Figure 4A:
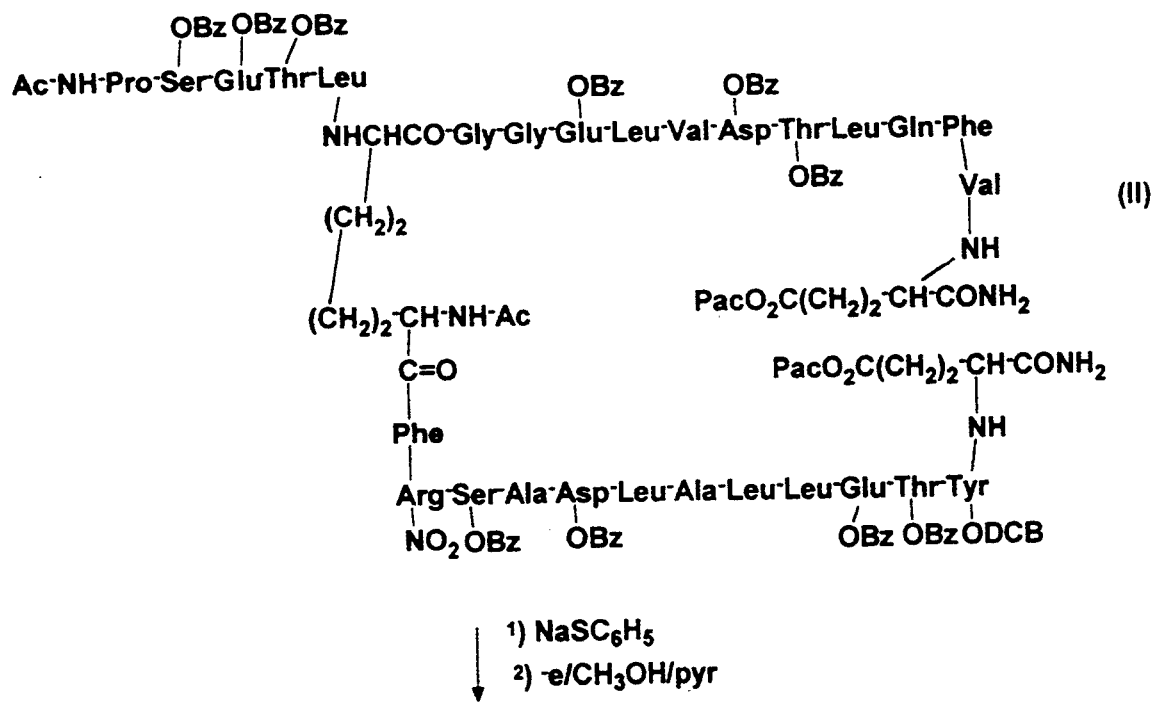
Figure 4B:
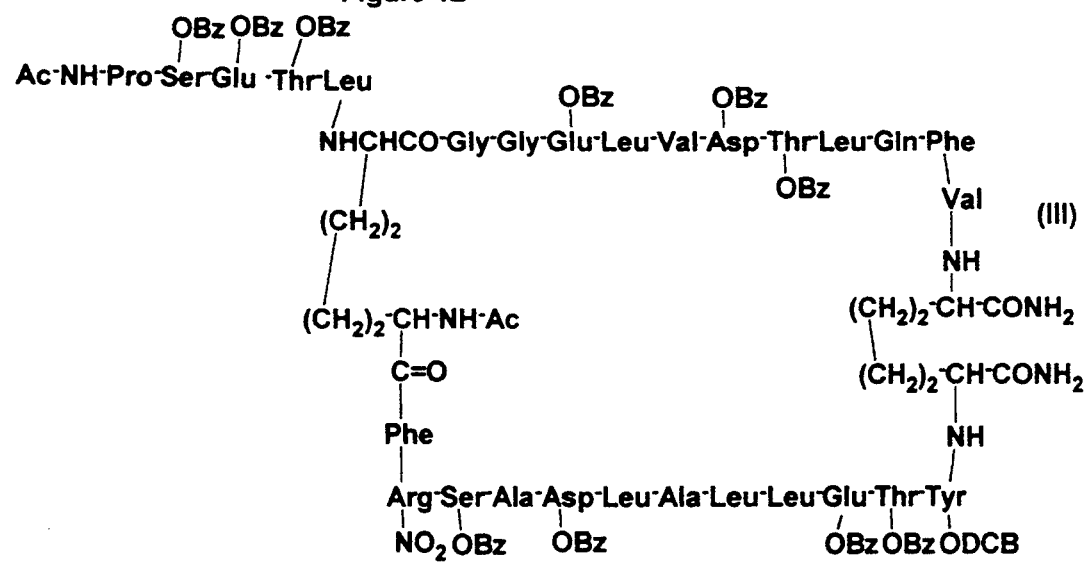
Figure 4B:
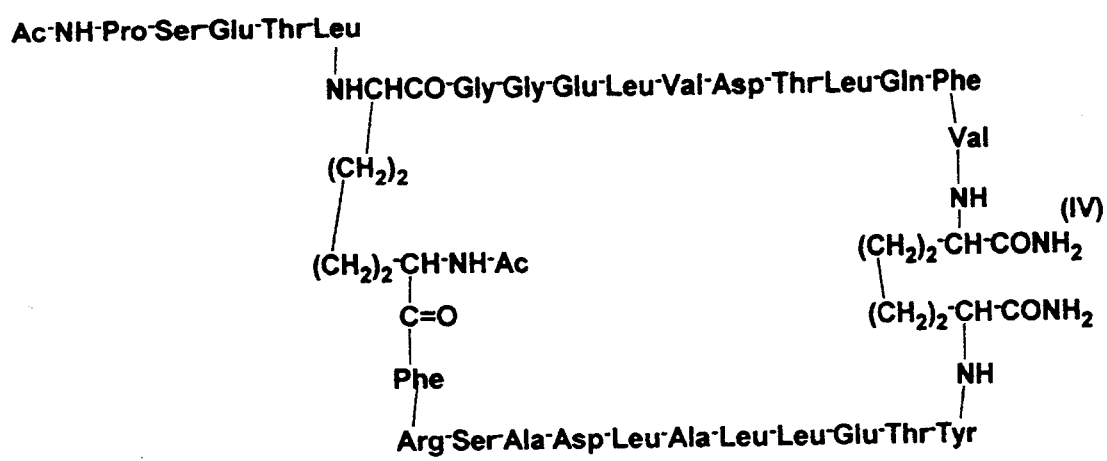

Active Analogues of Somatostatin (FIG. 3)

Electrochemical coupling techniques may be applied both in fragments from which model peptide hormones may be constructed by fragment condensation and also in whole peptide hormones. For the latter case, somatostatin analogues provide a second application of the cross-linking method with potential therapeutic significance. Somatostatin, a cyclic tetradecapeptide containing a Cys-Cys disulfide bridge, is a multifunctional regulatory hormone isolated from the hypothalamus. A previous cyclic somatostatin agonist which binds tightly to receptors in the anterior pituitary and inhibits growth hormone secretion (A. Gomez-Pan et al., Clin. Endocrinol. Metab. 12:469 (1983); P. Brazeau et al., Science 179:77 (1973)) has been observed to greatly slow the proliferation of solid tumors in human small cell lung carcinoma (J. E. Taylor et al., Biochem. Biophys, Res, Commun. 153:81 (1988)).

Redesign of agonists, such as those above, can be implemented using the methodology according to the present invention and will result in the development of a pharmacophore of greater activity and stability.

A dimethylene-bridged somatostatin-(2-15) analogue is prepared on a 2',4'-dimethoxy-4-benzhydrylamine resin using FMOC protocols (Fields, G. B. et al., supra) (see FIG. 3). The Lys residues will be protected with benzyloxycarbonyl (CBZ) groups, and Ser and Thr with benzyl groups. The Glu(gamma-t-Bu) side chain will be solvolyzed during the resin cleavage step, thereby preparing the electroactive moieties for the coupling step.

The Trp-8 residue, when protected by the 2,4-dichlorobenzyl-oxycarbonyl group (DCZ), will be stable to TFA, mild amine base, and electrooxidative conditions (Y. S. Klausner et al., J. Chem. Soc., Perkin Trans., I: 627 (1977)). After cleavage from the resin with TFA, the protected peptide amide will be oxidatively coupled, and deprotected under mild hydrogenolysis conditions (Pd-C, 4% HCOOH, MeOH). The bridged peptide will be purified by gel filtration on a Bio-Rad P-2 column and C-4 reverse phase HPLC.

NMR evidence (E. M. van den Berg et al., In: Peptides: Structure and Function, C. M. Deber et al., (eds), Pierce Chemical Co., Rockford, Ill., pp. 619ff (1987)) for β-turn formation stabilized by intramolecular hydrogen bonding between Thr-10(NH) and Phe-7(C=O) suggests a second model involving the insertion of Glu residues instead of Phe-6 and Phe-11. The hydrophobic dimethylene bridge will disrupt to a lesser extent the native hydrophobic interactions at these positions than will polar bridges.

EXAMPLE V

Active Analogs of Insulin and IGFs (FIG. 4)

First, in order to determine the functional domain(s) of the peptide, 20–30 residue fragments of the 67-residue IGF-II are prepared wherein each pair of Cys residues is replaced by Glu (G. B. Fields et al., Int. J. Peptide Protein Res. 35:161 (1990)). A second design includes partial replacement of Cys residues with Glu, making some bridges dimethylenes while others remain as disulfides. The Cys residues will be protected by standard methods (Fields et al., supra), such that they may be deprotected sequentially after the electrochemical coupling step. The reduction in molecular freedom due to the dimethylene bridges is expected to stabilize the overall conformational structure of the region. An insulin analogue can be similarly prepared, and is indeed a simpler procedure because of the presence of only two pairs of Cys residues.

A synthetic target involves a convergent double coupling of a differentially protected fragment which preserves portions of both A and B domains. The N-terminal tripeptide is deleted since des(1-30)IGF-I exhibits enhanced potency in promoting organ growth (C. Gillespie et al., *J. Endocrinol.* 127:401 (1990)). The Lys residues will be protected with CBZ groups, Ser and Thr with benzyl groups, and Tyr with didborobenzyl (DCB). t-Butyl esters of Glu will be cleaved during resin cleavage giving the C-terminal amide diacid, ready for the first electrochemical step. Asp and Glu residues uninvolved in bridge formation will be protected as benzyl esters. Phenacyl glutamic esters can then be cleaved selectively with thiophenol (C. C. Yang et al., *J. Org. Chem.* 41:1032 (1976)), making available the reacting moieties for the second electrochemical step. Finally, all remaining benzyl protecting groups can be removed at once under catalytic transfer hydrogenolysis conditions (FIG. 4).

The second strategy is based on crystallographic data on insulin which demonstrates the presence of helical structure in the A and B chain (T. L. Blundell et al., *Adv. Prot. Chem.* 26:279 (1972)), and on an examination of helical net diagrams of IGF which support the contention that several stretches have amphiphilic structure. Thus putative $\alpha$-helical stretches can be stabilized in the peptides by bridging [i,i+4] residues located on the presumed hydrophobic face of portions of the hormone predicted to be amphiphilic. Maintaining the secondary structures of synthetic fragments of IGF will allow a comparison of their relative activities and therefore provide information on function for each region.

EXAMPLE VI

Figure 5:
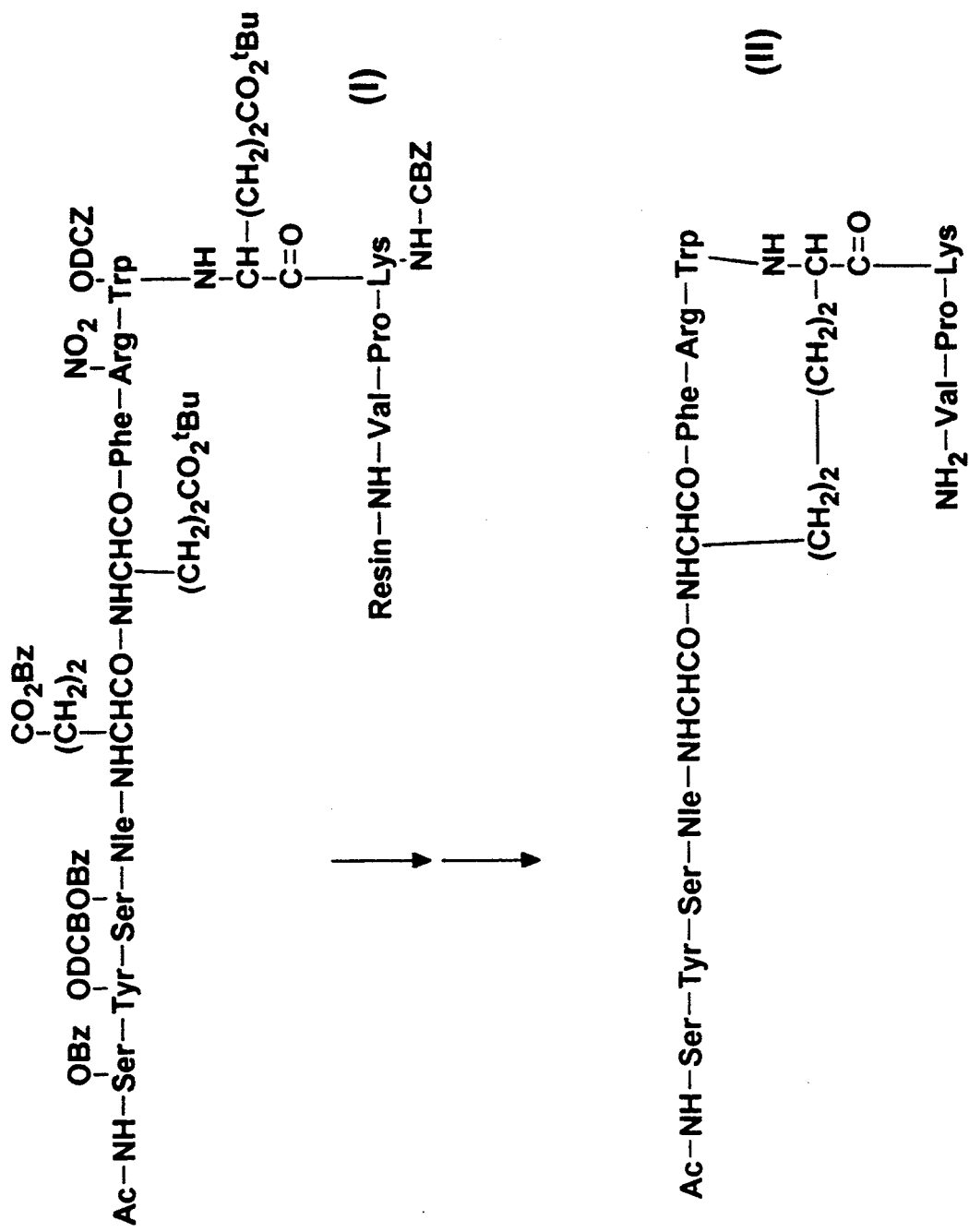
FIGS. 5-7 shows reaction sequences for synthesis of three different analogues of MSH (SEQ ID NO:5, SEQ ID NO:6, SEQ ID NO:7).
Figure 6:
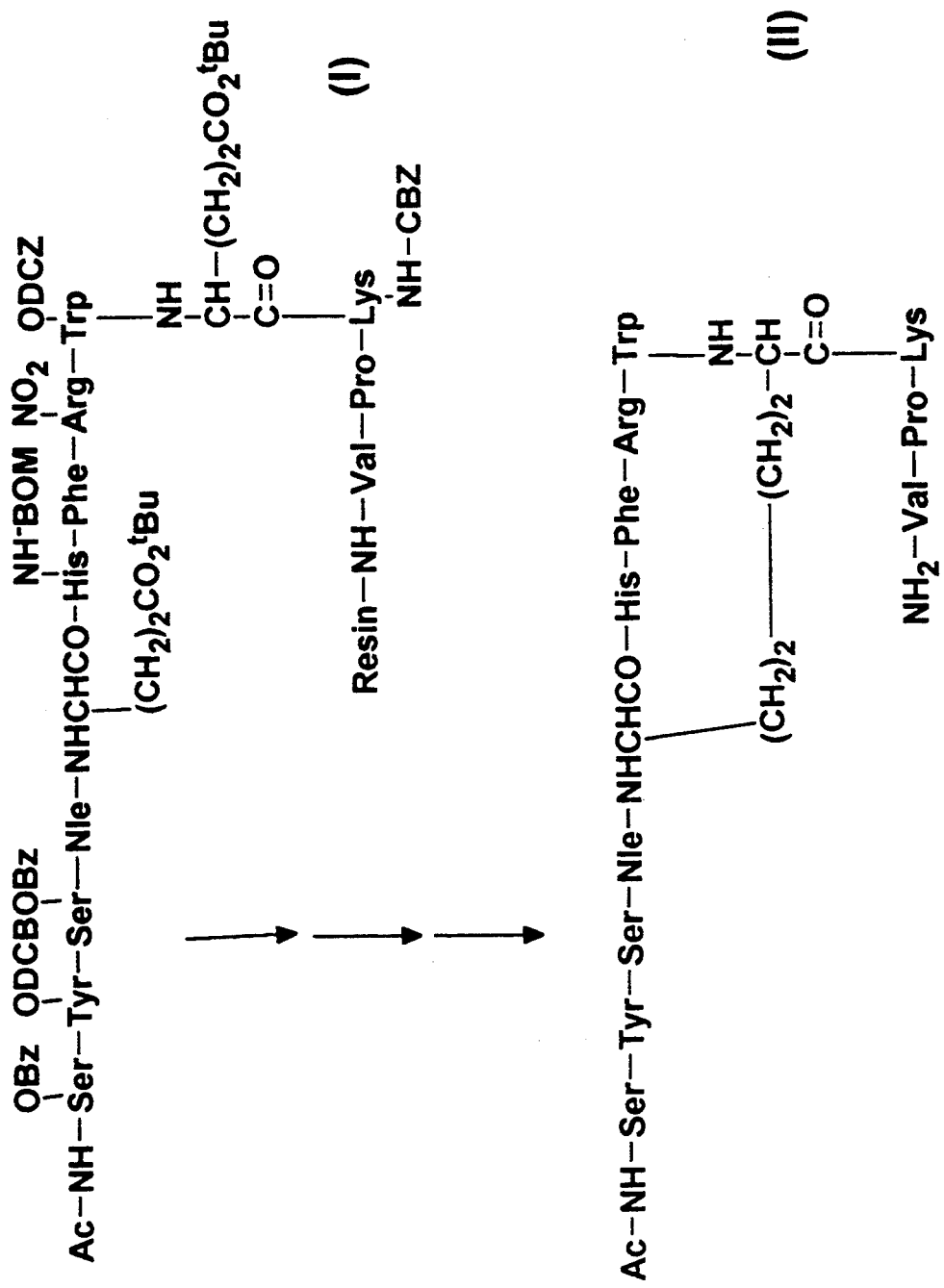
Figure 7:
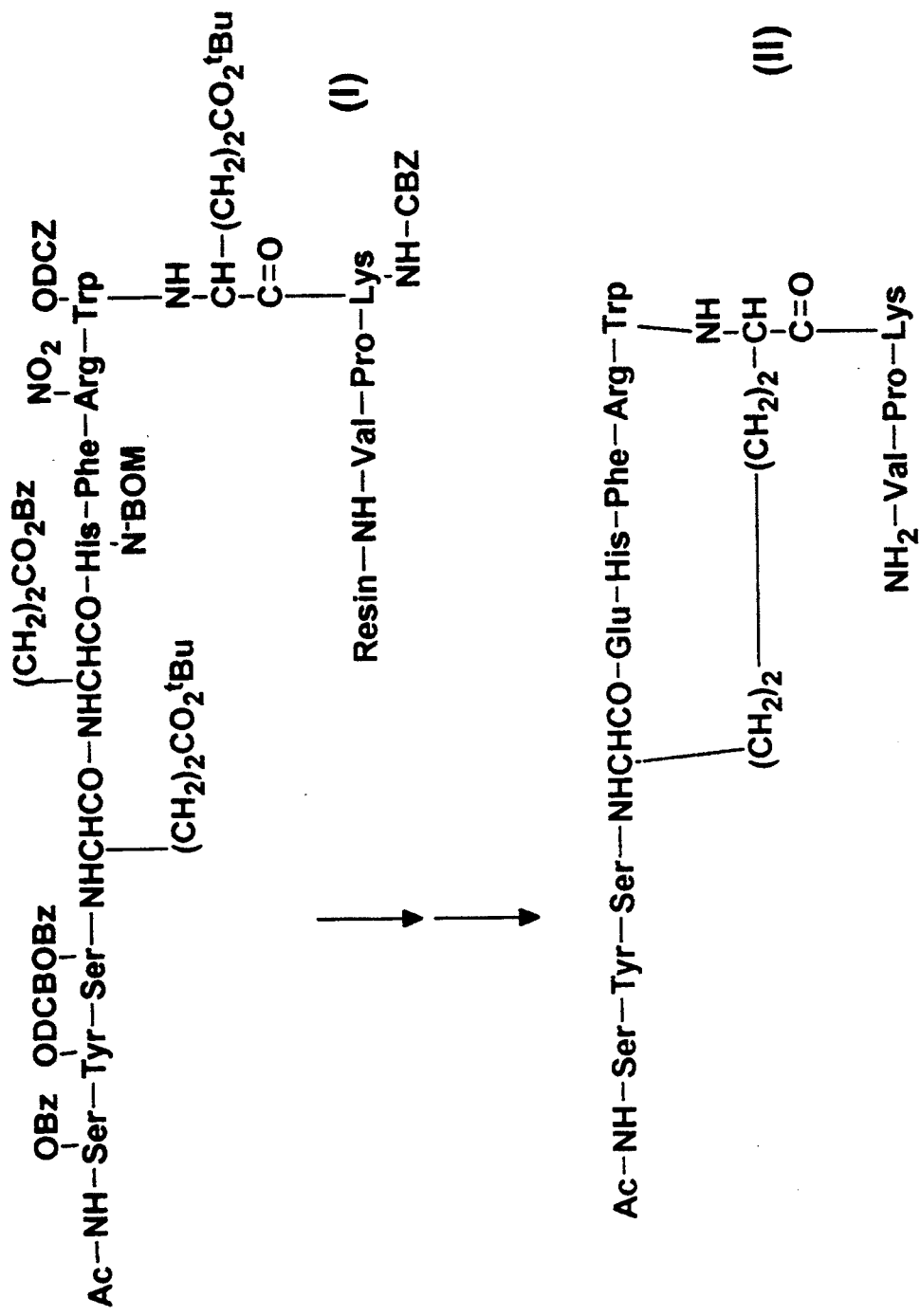

MSH Analogues (FIGS. 5-7)

Fragment studies have suggested that the region $\alpha$[7-9]MSH containing Phe-Arg-Trp constitutes the minimal necessary structural element for hormone activity. The bridging method used herein provides a simple strategy for restricting the conformation of this region. Initially, the conformation restricting linkage will be installed around this "active site" tripeptide. Three structures are shown in FIGS. 5-7. Each design entails a larger region about a putative active site, intended to access incrementally higher degrees of molecular flexibility.

EXAMPLE VII

Electrochemical Reductive Coupling of alpha,omega-dihalides

The electrochemical reductive coupling of alpha,omega-dihalides has generated nearly quantitative yields of strained rings. Serines and threonine residues protected by acid labile t-butyl groups can be selectively deprotected during the acid cleavage from the 2,4-dimethoxy(aminomethyl)-phenoxy resin. The hydroxyl group can be readily converted to chloride or bromide using $P(C_6H_6)_3/CX_4$ or $P(C_6H_6)_3Br_2$ without disturbing the normal functionalities present in peptides.

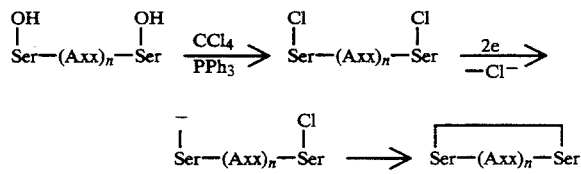

Reductive conditions of the otherwise protected dihalopeptide will lead to the corresponding cross-linked peptide.

For preparation of dihalopeptides, a solution of triphenylphosphine in acetonitrile is cooled in an ice bath and treated with slightly less than an equivalent amount of bromine (or other halogen) while stirring vigorously. The bis(serine) peptide (dialcohol) is dissolved in minimal dimethylformamide and added to the phosphine mixture over 5 minutes. Solvents are evaporated. The residue is taken up in ether, washed with sodium carbonate solution, and dried over magnesium sulfate. After solvents are removed, the residue is used directly in the coupling step.

A solution of dihalopeptide in acetonitrile/0.3M tetramethylammonium bromide is electrolyzed with the potential set at $-0.9$ to $-1.4V$ vs. Ag/AgCl (KCl) reference, and the temperature is kept at 20°-25° C. The electrolysis is terminated when the current falls below 10% of the initial value. After most of the acetonitrile is removed under vacuum, the residue is taken up into ether, washed with water, and purified by gel filtration and HPLC using conventional techniques.

In an alternative strategy, the hydroxyls are tosylated with TsCl/pyridine, and then followed by the electrochemical reduction to install an ether cross-linked bridge.

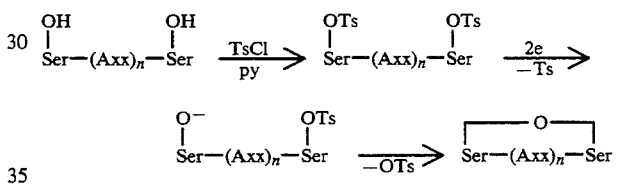

The oxyanion generated in situ is a convenient intermediate for increasing the length of the bridging tether by one bond. Amides, ethers, and esters are highly resistant to further electrochemical reduction.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A method for producing a conformationally restricted peptide or peptide isostere, comprising subjecting a peptide or peptide isostere having at least two amino acids or amino acid derivatives,
said amino acids or amino acid derivatives having side chains which can be coupled by means of an electrochemical coupling reaction,
to conditions sufficient to form a covalent bond between said side chains by means of an electrochemical coupling reaction.

2. A method according to claim 1, comprising:
(a) protecting any side chains of said amino acid or derivative which are not intended to take part in the electrochemical coupling reaction and which would otherwise be affected under the conditions of said reaction;
(b) subjecting said protected peptide or peptide isostere to conditions sufficient to cause an electrochemical coupling reaction between the side chains desired to be coupled, such conditions being insufficient to affect any of the remaining side chains of the peptide or peptide isostere; and
(c) deprotecting any said protected side chains.

3. A method according to claim 1 wherein said electrochemical coupling reaction is an oxidative coupling reaction.

4. A method according to claim 3 wherein said side chains comprise available carboxylic acid functional groups and said oxidative coupling reaction is the Kolbe reaction.

5. A method according to claim 3 wherein said side chains comprise an available first aliphatic amine group and a second amine group and said oxidative coupling reaction is the oxidative coupling of said aliphatic amine with said second amine forming a diazo linkage.

6. A method according to claim 3 wherein said side chains comprise available aromatic groups and said oxidative coupling reaction is the oxidative coupling of two aromatic rings.

7. A method according to claim 1 wherein said electrochemical coupling reaction is a reductive coupling reaction.

8. A method according to claim 7 wherein said side chains comprise available halo groups or available hydroxyl groups which are first converted into halo groups, and said coupling reaction is the reductive coupling of said two halo groups.

9. A method according to claim 7 wherein said side chains comprise available hydroxyl groups which are first substituted with alkyl- or arylsulfonyl groups, and said coupling reaction is the reductive coupling of said two alkyl- or arylsulfonyl groups through an ether cross-linked bridge.

10. A method according to claim 7 where in said side chains comprise nitrophenylalanine residues, and said coupling reaction is the reductive coupling of said nitrophenylalanine residues into a diazo linkage.

11. A method according to claim 1 wherein said peptide or peptide isostere has at least two cysteine residues, wherein, prior to said forming step, two cysteine residues are replaced with amino acids or amino acid derivatives having side chains capable of undergoing said electrochemical coupling reaction such that said covalent bond is formed between said two replacement amino acids or derivatives.

12. A method according to claim 1, useful for producing a stabilized alpha helical structure, wherein said peptide or peptide isostere has at least five amino acids or amino acid derivatives, wherein two amino acids or derivatives at position i and position i+4 have side chains capable of undergoing an electrochemical coupling reaction such that a covalent bond is formed between them.

13. A method according to claim 12 wherein the amino acids or amino acid derivatives at positions i+1, i+2 and i+3 are selected so as to permit an alpha helical structure to be obtained upon said coupling reaction.

14. A method according to claim 1, useful for producing a stabilized beta turn structure, wherein said peptide or peptide isostere has at least four amino acids or amino acid derivatives, wherein two amino acids or amino acid derivatives at positions i and i+3 have side chains capable of undergoing an electrochemical coupling reaction such that a covalent bond is formed between them.

15. A method according to claim 14 wherein the amino acids or amino acid derivatives at positions i+1 and i+2 are selected so as to permit a beta turn structure to be obtained upon said coupling reaction.

16. A method according to claim 14 wherein the amino acids at positions i+1 and i+2, respectively, are selected from the group consisting of Gly-Gly, Gly-Pro and Pro-Gly.

\* \* \* \* \*